(12) United States Patent
Sun et al.

(10) Patent No.: US 9,255,063 B2
(45) Date of Patent: Feb. 9, 2016

(54) COLCHICINE SOLID-STATE FORMS; METHODS OF MAKING; AND METHODS OF USE THEREOF

(71) Applicant: Takeda Pharmaceuticals U.S.A., Inc.

(72) Inventors: Tong Sun, Marlton, NJ (US); Kurt Nielsen, Chadds Ford, PA (US); Shawn Watson, Cherry Hill, NJ (US); Rolf Hilfiker, Allschwil (CH); Andreas Sieber, Bern (CH)

(73) Assignee: Takeda Pharmaceuticals U.S.A., Inc., Deerfield, IL (US)

( * ) Notice: Subject to any disclaimer, the term of this patent is extended or adjusted under 35 U.S.C. 154(b) by 105 days.

(21) Appl. No.: 13/646,931

(22) Filed: Oct. 8, 2012

(65) Prior Publication Data
US 2013/0116330 A1    May 9, 2013

Related U.S. Application Data

(62) Division of application No. 12/423,040, filed on Apr. 14, 2009, now Pat. No. 8,309,764.

(60) Provisional application No. 61/045,003, filed on Apr. 15, 2008.

(51) Int. Cl.
*A61K 31/16* (2006.01)
*C07D 233/00* (2006.01)
*C07C 233/32* (2006.01)

(52) U.S. Cl.
CPC ........... *C07C 233/32* (2013.01); *C07C 2103/34* (2013.01)

(58) Field of Classification Search
None
See application file for complete search history.

(56) References Cited

U.S. PATENT DOCUMENTS

| 3,329,694 | A | 7/1967 | Martel et al. |
| 4,760,092 | A | 7/1988 | Weinreb |
| 6,579,898 | B2 | 6/2003 | Humphrey |
| 8,003,700 | B2 | 8/2011 | Sun et al. |
| 2009/0093548 | A1 | 4/2009 | Davis et al. |

OTHER PUBLICATIONS

Terkeltaub "Colchicine Update: 2008" 2008 pp. 411-419.*
Cocco et al. "Colchicine in clinical medicine. A guide for internists" European Journal of Internal Medicine 2010 (21) 503-508.*
Eldad Ben-Chetrit and Micha Levy, Cochicine: 1998 Update, Siminars in Arthritis and Rheumatism, vol. 28, No. 1 (Aug. 1998): pp. 48-59.
International Search Report; International Application No. PCT/US2009/040462; International Filing Date Apr. 14, 2009; 3 pages.
Written Opinion of International Search Report; International Application No. PCT/US2009/040462; International Filing Date Apr. 14, 2009; 8 pages.
Mashahiro Nakano et al., "Solution and partition behaviors of colchicine", Chem. Pharm. Bull., 25(5), pp. 1109-1112 (1997).
J. V. Silverton, "Structure and absolute configuration, by several method, of (S)-2-O-acetyl-2-demethylthlocolchicine", Acta Cryst., C43, pp. 1802-1805 (1987).
Brossi, Arnold et al., "aS, 7S-absolute configuration of natural (−)-colchicine and allocongeners", FEBS Letters, 232(1), pp. 5-1 (1990).
King, Murray Vernon et al., X-ray diffraction determination of the chemical structure of colchicine, Acta Crystallographica, 5, pp. 437-440 (1952).
27650 Colchicine BioChemika, >96.0% (HPLC), 27650 Colchicine, http://www.sigmaaldrich.com/catalog/search/ProductDetail/FLUKA/27650?PrtPrv=1&I, Oct. 31, 2007, 4 pages.
Brues et al., CXCIV, Effects of Colchicine, Research Institute of the Royal Cancer Hospital (Free), London, S.W. 3.
Byrn et al., Pharmaceutical Solids: A Strategic Approach to Regulatory Considerations, Pharmaceutical Research, vol. 12, No. 7, 1995, 945-954.
C9754 Colchicine ~ 95% (HPLC), powder, http://www.sigmaaldrich.com/catalog/search/ProductDetail/SIGMA/C9754.
Colchicine, European Pharmacopeia 5.0, Jan. 2005, 1357-1359.
Kiselev et al., Methods of Isolating Alkaloids of the Colchicine Series, UDC 547.944.6, 502-509, 1991.
Needham et al., Total Pattern Analysis Using the New Organic Powder the New Organic Powder Diffraction File: PDF-4/Organics, American Pharmaceutical Review, 2003, 3 pages.
The Merck Index, 13th Edition, 2496, Colchicine, 2001, 3 pages.
USP 27, Colchicine, Official Monographs, Jan. 2004, 507-508.
Walaszek et al., Biosynthesis and Isolation of Radioactive Colchicinel Department of Pharmacology, University of Chicago, Chicago, Illinios, Aug. 29, 1952, 225-227.
Dominguez-Malagon HR et al., "Clinical and cellular effects of colchicine in fibromatosis," Cancer May 15, 1992; 69(10);2478-83 Abstract Only (1 page).
Imazio et al., "Colchicine Reduces Postoperative Atrial Fibrillation, Results of the Colchicine for the Prevention of the Postpericardiotomy Syndrome (COPPS) Atrial Fibrillation Substudy" Circulation. 2011; 124:2290-2295.
Kyle RA et al., "A trial of three regimens for primary amyloidosis: colchicine alone, melphalan and prednisone, and melphalan, prednisone, and colchicine," N Engl J Med. Apr. 24, 1997;336(17)1202-7 Abstract Only (1 page).
Lessinger, L., "The crystal structure of colchicine. A new application of magic integers to multiple-solution direct methods," Acta. Cryst. (1978) B34: 578-584.
Morissette, S. et al. "High-throughput crystallization: polymorphs, salts, co-crystals and solvates of pharmaceutical solids," Adv. Drug Delivery Reviews, (2004) 56: 275-300.

(Continued)

Primary Examiner — Jeffrey S Lundgren
Assistant Examiner — Michael Schmitt
(74) Attorney, Agent, or Firm — Foley & Lardner LLP

(57) ABSTRACT

Disclosed are new colchicine solid-state forms, methods of preparing the solid-state forms, as well as formulations prepared therefrom and uses thereof.

16 Claims, 24 Drawing Sheets

(56) References Cited

OTHER PUBLICATIONS

Schwarz YA et al., "A Clinical and Immunologic Study of Colchicine in Asthma," J Allergy Clin Immunol. Mar. 1990; 85(3):578-82; Abstract Only (1 page).

Sermet-Gaudelus et al., "Interest of colchicine for the treatment of cycstic fibrosis patents. Preliminary report." Mediators Inflamm. 1999; 8(1): 13-15.

The Merck Index, 12th ed., (1996), p. 5746.

* cited by examiner

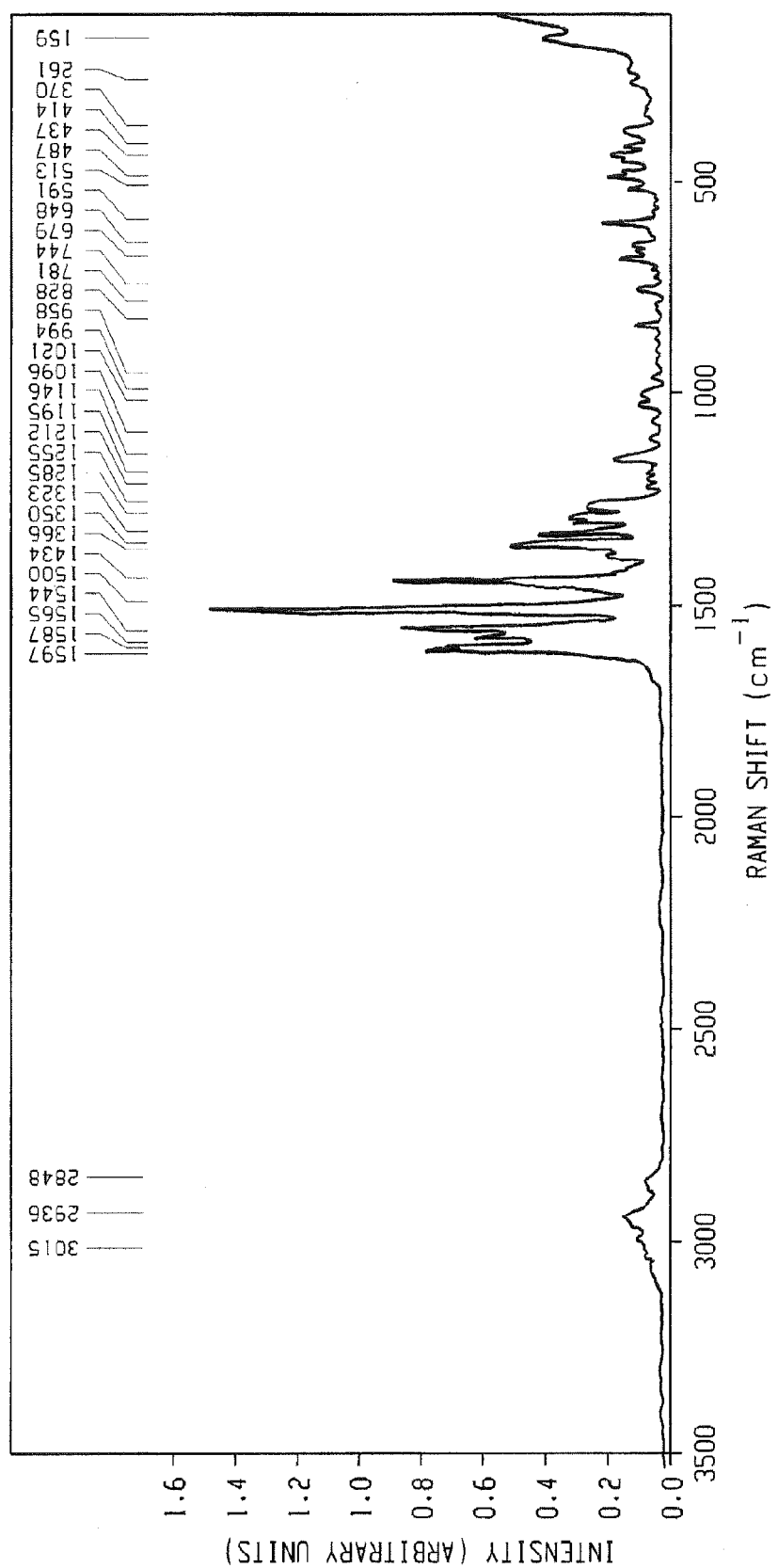

COLCHICINE SOLID-STATE FORMS; METHODS OF MAKING; AND METHODS OF USE THEREOF

CROSS REFERENCE TO RELATED APPLICATION

This application is a divisional application of U.S. application Ser. No. 12/423,040 filed Apr. 14, 2009, which claims the benefit of U.S. Provisional Application Ser. No. 61/045,003 filed Apr. 15, 2008, each of which is hereby incorporated by reference in its entirety.

BACKGROUND

Colchicine, chemical name (−)-N-[(7S,12aS)-1,2,3,10-tetramethoxy-9-oxo-5,6,7,9-tetrahydrobenzo[a]heptalen-7-yl]-acetamide, (N-((7S)-5,6,7,9-tetrahydro-1,2,3,10-tetramethoxy-9-oxobenzo[a]heptalen-7-yl)-acetamide, IUPAC), CAS Registry No. 64-86-8 is a known gout suppressant.

Polymorphs are solid crystalline phases of an active agent differing by the arrangement of the active agent molecules in the solid state. An active agent may also exist in other solid-state forms such as a hydrate, a solvate, or an ansolvate. The active agent may also exist in a non-crystalline or amorphous form. Different solid-state forms of the same active agent can exhibit different physical properties such as solubilities, melting points, hardness, optical properties, dissolution, and the like. Differences in the dissolution of the solid-state forms can result in differences in the therapeutic activity between the different forms.

Polymorphism and solid-state properties is an important consideration in formulating an active agent, specifically in regard to solubility of the active agent and dissolution from a dosage formulation. Use of a particular solid-state form may provide superior solubility, dissolution, and possibly increased bioavailability.

There remains a need in the art for new colchicine solid-state forms and processes of preparing such forms.

SUMMARY

In one embodiment, a solid-state colchicine is colchicine Form B cyclohexane solvate.

In another embodiment, a solid-state colchicine is colchicine Form C hydrate or Form K hydrate.

In yet another embodiment, a solid-state colchicine is colchicine Form D ethanol solvate.

In still another embodiment, a solid-state colchicine is colchicine Form E ansolvate.

In one embodiment, a solid-state colchicine is colchicine Form F non-crystalline.

In another embodiment, a solid-state colchicine is colchicine Form G acetone solvate.

In yet another embodiment, a solid-state colchicine is colchicine Form H dioxane solvate.

In still another embodiment, a solid-state colchicine is colchicine Form I tetrahydrofuran solvate.

In one embodiment, a solid-state colchicine is colchicine Form J toluene solvate.

In another embodiment, a solid-state colchicine is colchicine Form L mesitylene solvate.

In one embodiment, a composition comprises a solid-state colchicine selected from the group consisting of Form B, Form C, Form D, Form E, Form F, Form G, Form H, Form I, Form J, Form K, Form L, and a combination thereof; and a pharmaceutically acceptable excipient.

In another embodiment, a method of treating a patient comprises administering to a patient in need of colchicine therapy a composition comprising a solid-state colchicine selected from the group consisting of Form B, Form C, Form D, Form E, Form F, Form G, Form H, Form I, Form J, Form K, Form L, and a combination thereof; and a pharmaceutically acceptable excipient.

Also disclosed are methods of preparing solid-state forms of colchicine Forms B, C, D, E, F, G, H, I, J, K, and L.

These and other embodiments, advantages and features of the present invention become clear when detailed description and examples are provided in subsequent sections.

BRIEF DESCRIPTION OF DRAWINGS

FIG. 6 illustrates a FT-Raman spectrum of colchicine Form C.

DETAILED DESCRIPTION

Figure 1:
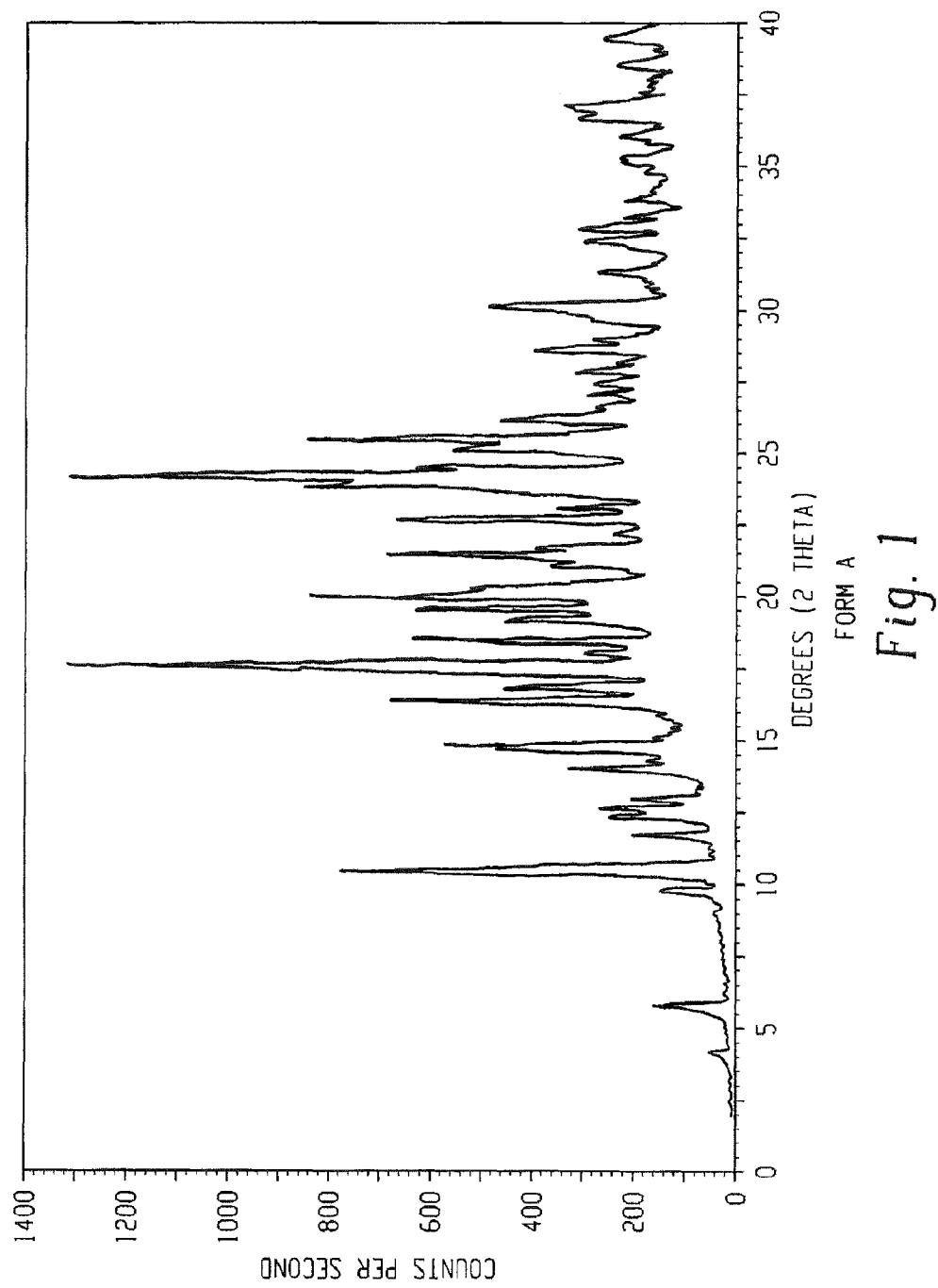
FIG. 1 illustrates XRPD pattern of colchicine Form A.

Disclosed herein are novel solid-state forms of colchicine described herein as Form B, Form C, Form D, Form E, Form F, Form G, Form H, Form I, Form J, Form K, and Form L. Known crystalline colchicine is designated as Form A, an ethyl acetate solvate containing 6.8% ethyl acetate. Also disclosed herein are methods of preparing the solid-state forms, compositions comprising the solid-state forms and methods of using the solid-state forms for treating a patient in need of colchicine therapy.

As used herein, "solid-state form" is inclusive of polymorphs, hydrates, solvates, ansolvates, and amorphous forms.

The solid-state forms of colchicine disclosed herein may be hydrated or solvated. The different forms may be characterized and differentiated on the basis of their X-ray powder diffraction (XRPD) peaks or FT-Raman peaks exemplified, for example, in the Tables in the Example section below. Solid state forms may also be differentiated by their melting point as determined by, for example, differential scanning calorimetry (DSC); by thermogravimetric analysis (TGA); by their FT-IR spectra; and by their crystalline unit cell parameters.

Colchicine Form B is a cyclohexane solvate. In one embodiment, colchicine Form B exhibits XRPD peak positions at 5.79, 10.50, 12.48, 14.73, 16.38, 17.47, 19.33, 19.78, 21.27, 22.57, 23.86, and 25.11±0.2 degrees 2-theta. In another embodiment, colchicine Form B exhibits the XRPD peak positions in Table 6 below. In yet another embodiment, colchicine Form B exhibits an X-ray powder diffraction pattern which is substantially similar to FIG. 3. In another embodiment, colchicine Form B exhibits Raman peaks at 2936, 1594, 1571, 1553, 1503, 1432, 1350, 1323, and 1286±2 $cm^{-1}$. In another embodiment, colchicine Form B exhibits Raman peaks in Table 6 below. In another embodiment, colchicine Form B exhibits a Raman spectrum which is substantially similar to FIG. 4. Form B can contain about 4.5 to about 7.0% cyclohexane, specifically about 5.0 to about 6.6%, more specifically about 5.4 to about 6.0%, and yet more specifically about 5.6% cyclohexane.

Cochicine Form C is a hydrate. In one embodiment, colchicine Form C exhibits XRPD peak positions at 10.11, 11.69, 13.35, 15.55, 16.61, 17.58, 17.93, 18.34, 19.44, 21.00, 21.42, 24.23, 24.91, 25.96, 27.38, 28.05, and 28.87±0.2 degrees 2-theta. In another embodiment, colchicine Form C exhibits the XRPD peak positions in Table 8 below. In yet another embodiment, colchicine Form C exhibits an X-ray powder diffraction pattern which is substantially similar to FIG. 5. In another embodiment, colchicine Form C exhibits Raman peaks at 2930, 1597, 1544, 1500, 1434, 1350, 1323, 1285, and 1254±2 $cm^{-1}$. In another embodiment, colchicine Form C exhibits Raman peaks in Table 8 below. In another embodiment, colchicine Form C exhibits a Raman spectrum which is substantially similar to FIG. 6. Not wishing to be bound by theory, colchicine C is likely a sesquihydrate. Form C can comprise about 5.5 to about 7.0% water, specifically about 5.8 to about 6.8, more specifically about 6.0 to about 6.5, and yet more specifically about 6.3% water. In one embodiment, Form C has a melting peak of about 115° C. by DSC analysis. In another embodiment, Form C is substantially free of solvent other than water.

Colchicine Form D is an ethanol solvate. In one embodiment, colchicine Form D exhibits XRPD peak positions at 9.45, 10.88, 13.63, 16.26, 18.31, 18.76, 21.16 and 25.10±0.2 degrees 2-theta. In another embodiment, colchicine Form D exhibits the XRPD peak positions in Table 10 below. In yet another embodiment, colchicine Form D exhibits an X-ray powder diffraction pattern which is substantially similar to FIG. 8. In another embodiment, colchicine Form D exhibits Raman peaks at 2933, 1588, 1569, 1549, 1501, 1443, 1436, 1352 and 1325±2 $cm^{-1}$. In another embodiment, colchicine Form D exhibits Raman peaks in Table 10 below. In another embodiment, colchicine Form D exhibits a Raman spectrum which is substantially similar to FIG. 9. Form D can comprise about 9.0 to about 11% ethanol, specifically about 9.4 to about 10.7%, and more specifically about 10 to about 10.3% ethanol. In one embodiment, Form D has a melting peak of about 95° C. by DSC analysis.

Colchicine Form D can be desolvated by drying under an inert atmosphere (e.g., nitrogen, argon, and the like) or under vacuum. In one embodiment, the drying can occur at about room temperature, specifically about 15 to about 30° C., more specifically about 18 to about 25° C., and yet more specifically about 20 to about 22° C. The resulting solid-state form is likely Form E ansolvate.

Colchicine Form E is an ansolvent. In one embodiment, colchicine Form E exhibits XRPD peak positions at 8.16, 9.79, 11.76, 13.13, 13.81, 15.60, 16.16, 17.79, 19.64, 20.36, 20.88, 22.00, 22.59, 23.67, 24.75, and 26.90±0.2 degrees 2-theta. In another embodiment, colchicine Form E exhibits the XRPD peak positions in Table 12 below. In yet another embodiment, colchicine Form E exhibits an X-ray powder diffraction pattern which is substantially similar to FIG. 10. In another embodiment, colchicine Form E exhibits Raman peaks at 2933, 1577, 1503, 1429, 1350, 1324, and 1280±2 $cm^{-1}$. In another embodiment, colchicine Form E exhibits Raman peaks in Table 12 below. In another embodiment, colchicine Form E exhibits a Raman spectrum which is substantially similar to FIG. 11. In one embodiment, Form E comprises about 0.00001% to about 2.5% solvent, specifically about 0.1 to about 2% solvent, and yet more specifically about 0.5 to about 1% solvent.

In one embodiment, colchicine Form F is a non-crystalline form of colchicine. In another embodiment, colchicine Form F exhibits an X-ray powder diffraction pattern which is substantially similar to FIG. 12. In another embodiment, colchicine Form F exhibits Raman peaks at 2934, 1586, 1504, 1430, 1351, 1323, and 1285±2 $cm^{-1}$. In another embodiment, colchicine Form F exhibits Raman peaks in Table 15 below. In another embodiment, colchicine Form F exhibits a Raman spectrum which is substantially similar to FIG. 13. In one embodiment, colchicine Form F can contain water.

Colchicine Form G is an acetone solvate. In one embodiment, colchicine Form G exhibits XRPD peak positions at 9.39, 12.01, 12.41, 16.44, 18.87, 19.67, 20.94, 22.28, 23.82, and 25.59±0.2 degrees 2-theta. In another embodiment, colchicine Form G exhibits the XRPD peak positions in Table 17 below. In yet another embodiment, colchicine Form G exhibits an X-ray powder diffraction pattern which is substantially similar to FIG. 14. In another embodiment, colchicine Form G exhibits Raman peaks at 2935, 1596, 1559, 1504, 1431, 1347, 1323, and 1292±2 $cm^{-1}$. In another embodiment, colchicine Form G exhibits Raman peaks in Table 17 below. In another embodiment, colchicine Form G exhibits a Raman spectrum which is substantially similar to FIG. 15. Form G can comprise about 10 to about 30% acetone, specifically about 12.7 to about 25% acetone, and more specifically about 15 to about 18.3% acetone. In one embodiment, Form G has a melting peak of about 87° C. by DSC analysis.

Colchicine Form H is a dioxane solvate. In one embodiment, colchicine Form H exhibits XRPD peak positions at 12.04, 13.32, 14.57, 15.78, 17.04, 18.05, 18.25, 20.35, 20.59, 22.00, 23.64, 24.13, and 24.35±0.2 degrees 2-theta. In another embodiment, colchicine Form H exhibits the XRPD peak positions in Table 19 below. In yet another embodiment, colchicine Form H exhibits an X-ray powder diffraction pattern which is substantially similar to FIG. 16. In another embodiment, colchicine Form H exhibits Raman peaks at 2940, 2846, 1573, 1503, 1442, 1430, 1353, 1324, and 1283±2 $cm^{-1}$. In another embodiment, colchicine Form H exhibits Raman peaks in Table 19 below. In another embodiment, colchicine Form H exhibits a Raman spectrum which is substantially similar to FIG. 17. In one embodiment, Form H comprises about 13 to about 22% dioxane, specifically about 15 to about 20%, and more specifically about 16 to about 18.1% dioxane.

Colchicine Form I is a tetrahydrofuran solvate. In one embodiment, colchicine Form I exhibits XRPD peak positions at 5.84, 9.86, 10.64, 11.74, 14.77, 16.45, 17.61, 19.10, 19.96, 21.44, 23.94, 24.12, 24.47, and 25.10±0.2 degrees 2-theta. In another embodiment, colchicine Form I exhibits the XRPD peak positions in Table 21 below. In yet another embodiment, colchicine Form I exhibits an X-ray powder diffraction pattern which is substantially similar to FIG. 18. In another embodiment, colchicine Form I exhibits Raman peaks at 2939, 2840, 1594, 1569, 1553, 1503, 1433, 1350, 1323, and 1286±2 cm$^{-1}$. In another embodiment, colchicine Form I exhibits Raman peaks in Table 21 below. In another embodiment, colchicine Form I exhibits a Raman spectrum which is substantially similar to FIG. 19. Form I can comprise about 5.0 to about 9.0% tetrahydrofuran, specifically about 5.7 to about 8.3%, and more specifically about 6.3 to about 7.0%.

Colchicine Form J is a toluene solvate. In one embodiment, colchicine Form J exhibits XRPD peak positions at 9.46, 10.43, 11.96, 13.27, 14.50, 15.67, 17.00, 18.10, 19.86, 20.43, 24.26, 25.62, 26.30, and 27.42±0.2 degrees 2-theta. In another embodiment, colchicine Form J exhibits the XRPD peak positions in Table 23 below. In yet another embodiment, colchicine Form J exhibits an X-ray powder diffraction pattern which is substantially similar to FIG. 20. In another embodiment, colchicine Form J exhibits Raman peaks at 3065, 2933, 1590, 1574, 1502, 1441, 1430, 1350, 1321, and 1283±2 cm$^{-1}$. In another embodiment, colchicine Form J exhibits Raman peaks in Table 23 below. In another embodiment, colchicine Form J exhibits a Raman spectrum which is substantially similar to FIG. 21. Form J can comprise about 14.0 to about 19.5% toluene, specifically about 15.0 to about 9.0%, and more specifically about 16.3 to about 18.7% toluene.

Colchicine Form K is probably a hydrate. In one embodiment, colchicine Form K exhibits XRPD peak positions at 11.95, 13.48, 13.59, 17.84, 18.09, 18.52, 21.61, 23.78, 25.16 and 27.65±0.2 degrees 2-theta. In another embodiment, colchicine Form K exhibits the XRPD peak positions in Table 25 below. In yet another embodiment, colchicine Form K exhibits an X-ray powder diffraction pattern which is substantially similar to FIG. 22. In another embodiment, colchicine Form K exhibits Raman peaks at 2931, 1597, 1587, 1565, 1544, 1500, 1435, 1350, 1323, 1297, and 1254±2 cm$^{-1}$. In another embodiment, colchicine Form K exhibits Raman peaks in Table 25 below. In another embodiment, colchicine Form K exhibits a Raman spectrum which is substantially similar to FIG. 23. Not wishing to be bound by theory, colchicine Form K is likely a dihydrate. Form K can comprise about 7.1 to about 9.0% water, specifically about 7.8 to about 8.7, more specifically about 8.0 to about 8.5, and yet more specifically about 8.3% water. In another embodiment, Form K is substantially free of solvent other than water.

Colchicine Form L is propably a mesitylene solvate. In one embodiment, colchicine Form L exhibits Raman peaks at 2935, 1591, 1570, 1553, 1503, 1432, 1349, 1323, and 1286±2 cm$^{-1}$. In another embodiment, colchicine Form L exhibits Raman peaks in Table 27 below. In another embodiment, colchicine Form L exhibits a Raman spectrum which is substantially similar to FIG. 24. Colchicine Form L can contain about 4.0 to about 10.0% mesitylene, specifically about 4.8 to about 9.1%, and more specifically about 6.0 to about 7.0% mesitylene.

In one embodiment, the colchicine solid-state form is a solvate of an International Conference on Harmonisation (ICH) class 3 solvent. Exemplary ICH class 3 solvents include acetic acid, acetone, anisole (methoxybenzene), 1-butanol, 2-butanol, butyl acetate, tert-butylmethyl ether, cumene (isopropylbenzene(1-methyl)ethylbenzene), dimethyl sulfoxide (DMSO), ethanol, 2-ethoxyethanol, ethyl acetate, ethyl ether, ethyl formate, formic acid, n-heptane, isobutyl acetate, isopropyl acetate, isopropyl alcohol, methyl acetate, 3-methyl-1-butanol (isoamyl alcohol), methylethyl ketone, methylisobutyl ketone, 2-methyl-1-propanol (isobutyl alcohol), n-pentane, 1-pentanol (amyl alcohol), and propyl acetate.

In one embodiment, the colchicine Form B, C, D, E, F, G, H, I, J, K or L is substantially free of impurities. "Substantially free of impurities" means a material comprises no more than about 4.0% total impurities, excluding any solvent that may be part of the specified solid-state form (e.g., for colchicine Form B cyclohexane solvate, cyclohexane is excluded as an impurity). In additional embodiments, the material comprises no more than about 3.0% total impurities, more specifically no more than about 2.0% total impurities, and yet more specifically no more than about 1.0% total impurities. Exemplary impurities include N-deacetyl-N-formyl colchicine (N-[(7S,12aS)-1,2,3,10-tetramethoxy-9-oxo-5,6,7,9-tetrahydrobenzo[a]heptalen-7-yl]formamide), β-Lumi-colchicine (N-[(7S,7bR,10aS)-1,2,3,9-tetramethoxy-8-oxo-5,6,7,7b,8,10a-hexahydrobenzo[a]cyclopenta[3,4]cyclobuta[1,2-c]cyclohepten-7-yl]-acetamide), Colchicoside (N-[(7S,12aS)-3-(β-D-glucopyranosyloxy)-1,2,10-trimethoxy-9-oxo-5,6,7,9-tetrahydrobenzo[a]heptalen-7-yl]-acetamide), 3-O-demethyl colchicine (N-[(7S,12aS)-3-hydroxy-1,2,10-trimethoxy-9-oxo-5,6,7,9-tetrahydrobenzo[a]heptalen-7-yl]-acetamide), and colchiceine (N-[7S,12aS)-10-hydroxy-1,2,3-trimethoxy-9-oxo-5,6,7,9-tetrahydrobenzo[a]heptalen-7-yl]acetamide).

The purity of the colchicine can be determined using a variety of techniques known in the art such as high pressure liquid chromatography (HPLC), and the like.

The solid-state forms of colchicine can be prepared using a variety of techniques including crystallization from solution and precipitation from solution using an antisolvent, suspension equilibration ("slurrying"), drying and water vapor adsorption, and evaporation. The foregoing processes, or any isolation step or drying step, can be carried out under ambient conditions or under an inert atmosphere (e.g., nitrogen, argon, and the like).

The starting colchicine material for the following processes can be any one of Forms A, B, C, D, E, F, G, H, I, J, K, L, a solvate, a hydrate, or a mixture thereof.

New processes of preparing colchicine include crystallization from a solvent system containing a single solvent or two or more solvents. Optionally, an anti-solvent can be used.

In a generalized procedure, colchicine is dissolved in a solvent system with optional heating to form a crystallization solution. In one embodiment, the heated solution can be at about the boiling point of the solvent system, specifically about 25 to about 100° C., more specifically about 30 to about 90° C., yet more specifically about 40 to about 80° C., and still yet more specifically about 50 to about 70° C.

The crystallization solution can be allowed to stand at ambient temperature or cooled to a lower temperature to allow crystal formation. In one embodiment, temperatures for crystal formation can be about −20 to about 25° C., specifically about −10 to about 20° C., more specifically about 0 to about 15° C., and yet more specifically about 3 to about 10° C.

The crystallization can be accomplished with slow cooling or rapid cooling. Rapid cooling can involve placing the crystallization solution under conditions of the targeted lower temperature without a gradual lowering of the temperature. In one embodiment, slow cooling can involve reducing the temperature of the crystallization solution at about 1 to about 30° C. per hour, specifically about 5 to about 25° C. per hour, and yet more specifically about 10 to about 20° C. per hour to a targeted lower temperature.

Optionally, the crystallization solution, prior to any solids formation, can be filtered to remove any undissolved solids, solid impurities and the like prior to removal of the solvent. Any filtration system and filtration techniques known in the art can be used.

In one embodiment, the crystallization solutions can be seeded with the desired solid-state form of colchicine.

Suitable solvents for preparing the solid-state forms of colchicine include those that do not adversely affect the stability of the colchicine, and are preferably inert. Suitable solvents may be organic, aqueous, or a mixture thereof. Suitable organic solvents may be an aqueous solvent such as water or water combined with a water miscible solvent; aliphatic hydrocarbons such as n-octane and cyclohexane; aliphatic alcohols such as methanol (MeOH), ethanol (EtOH), n-propanol, isopropanol (IPA), n-butanol, tert-amyl alcohol (t-AmOH); ethers such as tetrahydrofuran (THF), dioxane, methyl-tert-butyl ether, 1,2-dimethoxyethane (DME), and 2-methyl tetrahydrofuran; aliphatic ketones such as acetone, methyl ethyl ketone (MEK), and methyl isobutyl ketone; aliphatic carboxylic esters such as methyl acetate, ethyl acetate (EtOAc), and isopropyl acetate; aromatic hydrocarbons such as benzene, toluene, xylene, and mesitylene; aliphatic hydrocarbons such as hexane; aliphatic nitriles such as acetonitrile (MeCN); chlorinated hydrocarbons such as dichloromethane (DCM), chloroform, and carbon tetrachloride; aliphatic sulfoxides such as dimethyl sulfoxide (DMSO); amides such as dimethylformamide (DMF) and dimethylacetamide (DMA); organic acids such as acetic acid; N-methyl-2-pyrrolidone; pyridine; and the like, as well as mixtures comprising at least one of the foregoing organic solvents. Other solvents can be used as an anti-solvent to induce crystal formation of the colchicine from solution.

"Solvent system" means a single or a combination of two or more solvents.

In one embodiment, Form B can be prepared by dissolving colchicine in a mixture of cyclohexane and ethanol with optional heating. An amount of cyclohexane is added to the solution as an antisolvent such that Form B precipitates from solution. In one embodiment, the temperature of the mixture for the precipitation process can be about room temperature to about 80° C., specifically about to about 70° C., and yet more specifically about 40 to about 60° C. The starting colchicine can be Form A.

In one embodiment, Form D can be prepared by dissolving colchicine in a mixture of n-octane and ethanol with optional heating. An amount of n-octane is added to the solution as an antisolvent such that Form D precipitates from solution. The temperature of the mixture for the precipitation process can be about room temperature to about 80° C., specifically about 30 to about 70° C., and yet more specifically about 40 to about 60° C.

Suspension equilibration, or "slurrying", as opposed to complete dissolution of colchicine in a solvent system, can be used to prepare a colchicine solid-state form. For example a suspension of colchicine can be prepared by combining colchicine and a solvent system wherein some of the colchicine is not fully dissolved. Solvents and solvent system as previously discussed can be applied here.

Processes of preparing colchicine include slurrying a mixture of colchicine and a solvent system containing a single solvent or two or more solvents. Optionally, an anti-solvent can be used. The volume of the solvent system used to prepare the slurry mixture is an amount such that the colchicine is not fully dissolved.

In one embodiment, the slurry mixture can be heated to about the boiling point of the solvent system, specifically about 25 to about 100° C., more specifically about 30 to about 90° C., yet more specifically about 40 to about 80° C., and still yet more specifically about 50 to about 70° C.

Optionally, slurry mixture can be allowed to stand at ambient temperature or cooled to a lower temperature to allow solid formation. In one embodiment, slurrying temperatures can be about −20 to about 25° C., specifically about −10 to about 20° C., more specifically about 0 to about 15° C., and yet more specifically about 3 to about 10° C.

The slurry mixture can initially be heated followed by slow cooling or rapid cooling. Rapid cooling can involve placing the slurry mixture under conditions of the targeted lower temperature without a gradual lowering of the temperature. In one embodiment, slow cooling can involve reducing the temperature of the slurry mixture at about 1 to about 30° C. per hour, specifically about 5 to about 25° C. per hour, and yet more specifically about 10 to about 20° C. per hour to a targeted lower temperature.

In one embodiment, the slurry mixture can be seeded with the desired solid-state form of colchicine.

Suitable solvents for preparing the solid-state forms of colchicine via slurrying include those discussed above.

Optionally, the slurry mixture can be sonicated.

In one embodiment, colchicine Form D is prepared by slurrying colchicine in ethanol, specifically cyclohexane/ethanol. In one embodiment, the slurrying can be performed at a temperature of about 0 to about 40° C., specifically about 10 to about 30° C. and yet more specifically about 20 to about 25° C. In another embodiment, the volume of the solvent system used to prepare the slurry mixture is an amount of about to about 100 mg to about 2 grams of colchicine per ml solvent, specifically about 200 mg to about 1 gram, and yet more specifically about 400 mg to about 800 mg per ml solvent. In one embodiment, the slurry mixture is seeded with Form D.

In one embodiment, colchicine Form G is prepared by slurrying colchicine in acetone. In one embodiment, the slurrying can be performed at a temperature of about 0 to about 40° C., specifically about 10 to about 30° C. and yet more specifically about 20 to about 25° C. In another embodiment, the volume of the solvent system used to prepare the slurry mixture is an amount of about to about 100 mg to about 1.5 grams of colchicine per ml solvent, specifically about 150 mg to about 1 gram, and yet more specifically about 200 mg to about 800 mg per ml solvent. In one embodiment, the slurry mixture is seeded with Form G.

In one embodiment, colchicine Form H is prepared by slurrying colchicine in 1,4-dioxane. in one embodiment, the slurrying can be performed at a temperature of about 0 to about 40° C., specifically about 10 to about 30° C. and yet more specifically about 20 to about 25° C. In another embodiment, the volume of the solvent system used to prepare the slurry mixture is an amount of about to about 100 mg to about 2 grams of colchicine per ml solvent, specifically about 200 mg to about 1 gram, and yet more specifically about 400 mg to about 800 mg per ml solvent. In one embodiment, the slurry mixture is seeded with Form H.

In one embodiment, colchicine Form I is prepared by slurrying colchicine in tetrahydrofuran. In one embodiment, the slurrying can be performed at a temperature of about 0 to about 40° C., specifically about 10 to about 30° C. and yet more specifically about 20 to about 25° C. In another embodiment, the volume of the solvent system used to prepare the slurry mixture is an amount of about to about 100 mg to about 2 grams of colchicine per ml solvent, specifically about 200 mg to about 1 gram, and yet more specifically about 400 mg to about 800 mg per ml solvent. In one embodiment, the slurry mixture is seeded with Form I.

In one embodiment, colchicine Form J is prepared by slurrying colchicine in toluene, specifically toluene/acetonitrile. In one embodiment, the slurrying can be performed at a temperature of about 0 to about 40° C., specifically about 10 to about 30° C. and yet more specifically about 20 to about 25° C. In another embodiment, the volume of the solvent system used to prepare the slurry mixture is an amount of about to about 100 mg to about 2 grams of colchicine per ml solvent, specifically about 200 mg to about 1 gram, and yet more specifically about 400 mg to about 800 mg per ml solvent. In one embodiment, the slurry mixture is seeded with Form J.

In the evaporation processes to prepare a colchicine solid-state form, colchicine can be dissolved in a solvent system and the solvent system can be allowed to evaporate until the colchicine solid-state form is formed. Heating or cooling as discussed previously can optionally be used. The solvent system can evaporate under vacuum conditions. Optionally, the evaporation can be accomplished under ambient conditions or under an inert atmosphere as discussed herein.

In one embodiment, colchicine Form C is prepared by suspending colchicine in 0.1 M tris(hydroxymethyl)-aminomethane solution and allowing the solvent to evaporate until Form C forms.

In one embodiment, Form K is prepared by suspending colchicine in 0.05 M tris(hydroxymethyl)-aminomethane buffer substance pH=7.4 and allowing the solvent to evaporate until Form K forms.

In the drying process, colchicine is placed under conditions to effect removal of any water or other solvent present. The removal can be accomplished under reduced pressure (e.g., vacuum) and optionally with heat.

In one embodiment, colchicine Form D is dried under nitrogen for a period of time sufficient to result in the conversion to colchicine Form E.

In one embodiment, colchicine Form C is prepared by exposing colchicine to greater than about 75% RH for a time sufficient to convert colchicine to Form C. In another embodiment, the colchicine starting material is slurried in water prior to isolation and subsequent exposure to greater than about 75% RH. The starting colchicine can be Form A, B, D, E, F, G, H, I, J, L or a colchicine solvate.

In any of the foregoing processes, the resulting solid colchicine can be isolated or dried under ambient conditions or under an inert atmosphere (e.g., nitrogen, argon, and the like). The drying can optionally be under vacuum. Furthermore, the drying can be accomplished with optional heating.

Also disclosed herein are pharmaceutical compositions comprising the colchicine solid-state forms prepared herein.

Solid dosage forms for oral administration include, but are not limited to, capsules, tablets, powders, and granules. In such solid dosage forms, the solid complex may be admixed with one or more of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, and combinations comprising one or more of the foregoing additives. For capsules and tablets, the dosage forms may also comprise buffering agents.

By "oral dosage form" is meant to include a unit dosage form for oral administration. An oral dosage form may optionally comprise a plurality of subunits such as, for example, microcapsules or microtablets. Multiple subunits may be packaged for administration in a single dose.

By "subunit" is meant to include a composition, mixture, particle, pellet, etc., that can provide an oral dosage form alone or when combined with other subunits.

The compositions can be immediate-release forms or controlled-release forms.

By "immediate-release" is meant a conventional or non-modified release in which greater then or equal to about 75% of the active agent is released within two hours of administration, specifically within one hour of administration.

By "controlled-release" is meant a dosage form in which the release of the active agent is controlled or modified over a period of time. Controlled can mean, for example, sustained-, delayed- or pulsed-release at a particular time. Alternatively, controlled can mean that the release of the active agent is extended for longer than it would be in an immediate-release dosage form, e.g., at least over several hours.

Dosage forms can be combination dosage forms having both immediate-release and controlled-release characteristics, for example, a combination of immediate-release pellets and controlled-release pellets. The immediate-release portion of a combination dosage form may be referred to as a loading dose.

Certain compositions described herein may be "coated". The coating may be a suitable coating, such as, a functional or a non-functional coating, or multiple functional or non-functional coatings. By "functional coating" is meant to include a coating that modifies the release properties of the total composition, for example, a sustained-release coating. By "non-functional coating" is meant to include a coating that is not a functional coating, for example, a cosmetic coating. A non-functional coating can have some impact on the release of the active agent due to the initial dissolution, hydration, perforation of the coating, etc., but would not be considered to be a significant deviation from the non-coated composition.

Also disclosed are methods of treating a patient in need of colchicine therapy with the colchicine solid-state forms. The colchicine solid-state forms disclosed herein and compositions prepared therefrom can be used in prevention or treatment of various diseases or conditions, including, for example, attacks of acute gouty arthritis and pain in attacks of acute gouty arthritis, chronic gout (prophylaxis), a cystic disease, for example polycystic kidney disease or cystic fibrosis, a lentiviral infection, demyelinating diseases of central or peripheral origin, multiple sclerosis, cancer, an inflammatory disorder such as rheumatoid arthritis, glaucoma, Dupuytren's contracture, idiopathic pulmonary fibrosis, primary amyloidosis, recurrent pericarditis, acute pericarditis, asthma, post-pericardiotomy syndrome, proliferative vitreoretinopathy, Behcet's disease, Familial Mediterranean fever, idiopathic thrombocytopenic purpura, primary biliary cirrhosis, and pyoderma gangrenosum, or in enhancing bone formation or bone mineral density.

The following examples further illustrate the invention but, of course, should not be construed as in any way limiting its scope.

EXAMPLES

The following experimental procedures are used unless stated otherwise.

The X-ray powder diffraction (XRPD) patterns are recorded with a PANalytical X'Pert powder diffractometer (Copper Ku radiation). Sample holder: metallic, sample thickness 0.4 mm. The sample is covered with Kapton foil (resulting in a slightly higher background). For X-ray measurements a hermetically closed sample chamber is used. The XRPD patterns are shown in the 2θ range from 2 to 400.

Fourier-transform Raman spectroscopy (FT-Raman) spectra are recorded on a Bruker RFS 100 FT-Raman system with a near infrared Nd:YAG laser operating at 1064 nm and a liquid nitrogen-cooled germanium detector. For each sample, 64 scans with a resolution of 4 cm$^{-1}$ are accumulated. 300 mW laser power is used. Raman measurements are conducted using hermetically closed glass tubes. The FT-Raman data are shown in the region between 3200 to 100 cm$^{-1}$. No peaks were measured from 3500 to 3200 cm$^{-1}$.

Thermogravimetry coupled with Fourier-transform infrared spectroscopy (TG-FTIR): Thermo gravimetric measurements are carried out with a Netzsch Thermo-Microbalance TG 209 coupled to a Bruker FTIR Spectrometer Vector 22 or IFS 28 (sample pans with a pinhole, N$_2$ atmosphere, heating rate 10 K/min, range 25° C. to 350° C.).

Dynamic vapor sorption (DVS): Sorption Measurement System SPS11-100n. The sample was placed in an Al crucible, and the sample was allowed to equilibrate at 75% relative humidity (RH) before starting a pre-defined humidity program.

$^1$H-NMR: $^1$H-NMR spectra were recorded using a Bruker DPX300 spectrometer with a proton frequency of 300.13 MHz, a 30° excitation pulse, and a recycle delay of 1 s. 16 scans were accumulated, and CDCl$_3$ was used as the solvent.

DSC: Differential scanning calorimetry was carried out with a Perkin Elmer DSC-7 instrument (closed gold sample pan or gold-plated steel sample pan; heating rates 10° C./min).

Example A

Characterization of Colchicine Form A, Ethyl Acetate Solvate

Colchicine Form A ethyl acetate solvate was analyzed by FT-Raman, XRPD and TG-FTIR and determined to be an ethyl acetate solvate containing about 6.8% ethyl acetate.

Figure 2:
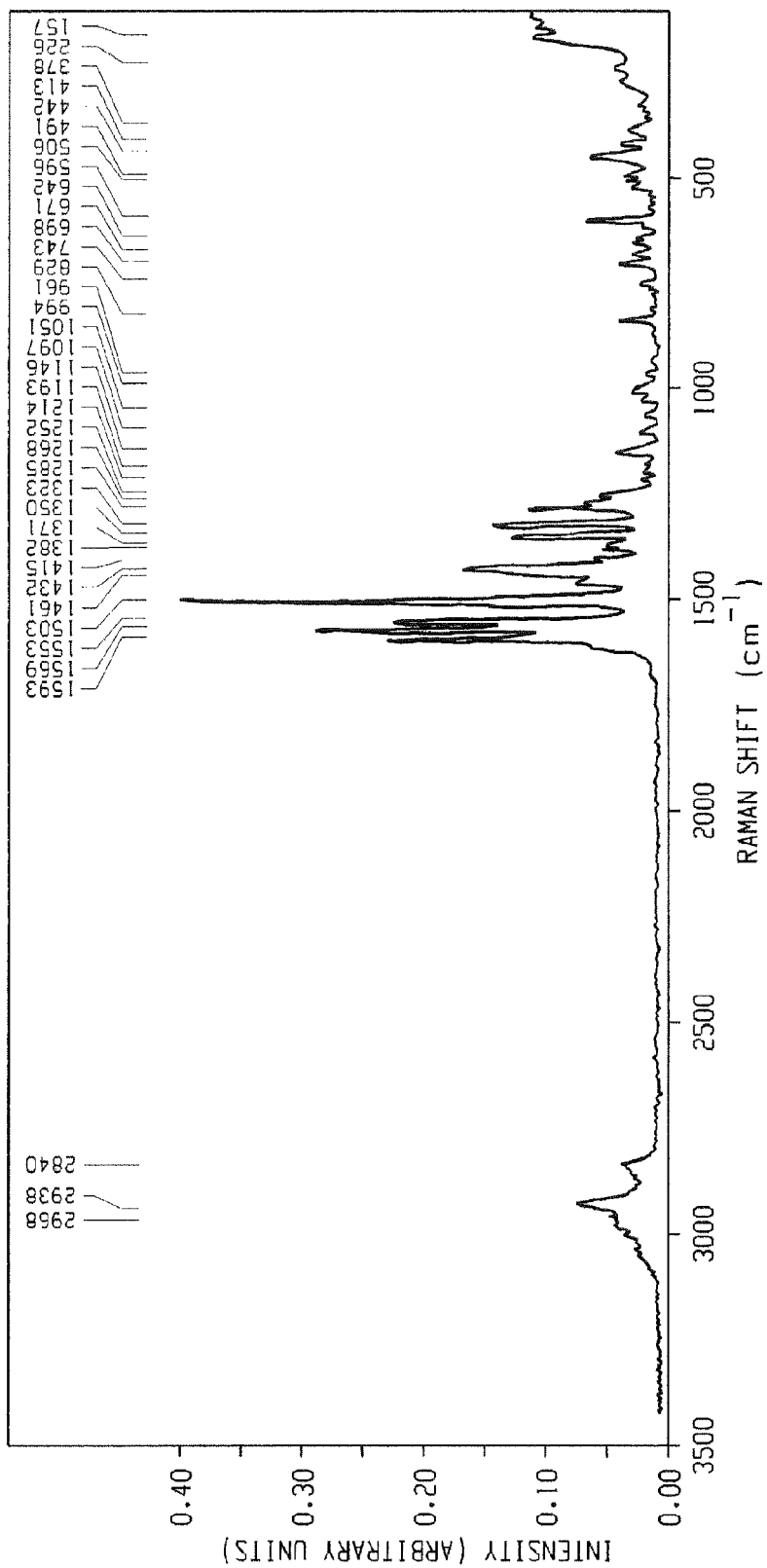
FIG. 2 illustrates a FT-Raman spectrum of colchicine Form A.

FIG. 1 illustrates an XRPD pattern of Form A with a peak listing provided in Table 1 below. FIG. 2 illustrates a FT-Raman spectrum and a peak listing is provided in Table 1.

TABLE 1

XRPD and FT-Raman peak table of colchicine Form A

| XRPD peaks | | FT-Raman peaks |
|---|---|---|
| 2θ [°] | Intensity [%] | (cm$^{-1}$) |
| 4.25 | 4 | 2968 |
| 5.82 | 10 | 2938 |
| 9.80 | 12 | 2840 |
| 10.58 | 56 | 1593 |
| 11.68 | 15 | 1569 |
| 12.37 | 17 | 1553 |
| 12.61 | 20 | 1503 |
| 12.94 | 15 | 1461 |
| 14.06 | 24 | 1432 |
| 14.89 | 41 | 1415 |
| 16.41 | 49 | 1382 |
| 16.84 | 34 | 1371 |
| 17.63 | 98 | 1350 |
| 18.07 | 20 | 1323 |
| 18.44 | 46 | 1285 |
| 19.04 | 33 | — |
| 19.45 | 46 | — |
| 19.96 | 61 | — |
| 20.23 | 35 | — |
| 21.03 | 27 | — |
| 21.44 | 51 | — |
| 21.70 | 28 | — |
| 22.70 | 49 | — |
| 23.08 | 27 | — |
| 23.57 | 31 | — |
| 23.91 | 64 | — |
| 24.15 | 100 | — |
| 24.40 | 47 | — |
| 24.97 | 42 | — |
| 25.43 | 64 | — |
| 26.14 | 34 | — |
| 26.96 | 22 | — |
| 27.45 | 21 | — |
| 27.85 | 25 | — |
| 28.53 | 31 | — |
| 28.81 | 21 | — |
| 29.67 | 22 | — |
| 30.12 | 38 | — |
| 31.28 | 19 | — |
| 32.33 | 23 | — |
| 32.81 | 24 | — |
| 33.18 | 16 | — |
| 33.81 | 17 | — |

TG-FTIR analysis reveals two stepwise weight losses for a total of 6.8% ethyl acetate, which are strongest at about 170 and about 240° C. This is typical for a solvate (3:1 colchicine to solvent). Decomposition is observed above 275° C.

TABLE 2

| Temperature range | Mass loss (%) | Released compound/comment |
|---|---|---|
| 25-200° C. | 4.44 | Ethyl acetate |
| 200-275° C. | 2.34 | Ethyl acetate |
| 275-350° C. | 9.18 | Decomposition |

Example B

Screening Experiments

Five techniques are used to find colchicine solid forms: 1) suspension equilibration, 2) precipitation 3) drying and water vapor adsorption, 4) evaporation, and 5) melt quench. Suspension equilibration generally is carried out by slurrying the colchicine in a solvent system, optionally including an anti-solvent. Precipitation generally is carried out by adding an antisolvent to a solution of colchicine. Evaporation technique is generally carried out by allowing the solvent of a solution of colchicine to evaporate to induce crystallization of the colchicine. Water vapor adsorption technique generally involves exposing colchicine to a controlled humid environment so that the material takes up water. The drying experiments can be performed under inert atmospheres (e.g., nitrogen). Melt quench generally involves fast cooling a melt to form a solid.

TABLE 3

Suspension equilibration results

| Starting material | Process | Solvent | Temperature (° C.) | Time stirred (days) | Outcome/remarks |
|---|---|---|---|---|---|
| Form A | Slurry, isolated; drying | Water | Room temp. | 2 | Analyzed by FT-Raman/dried at 0% RH |
| Form A | Slurry, isolated; water vapor adsorption | Water | Room temp. | 2 | Form C/dried at 75.5% RH 3 weeks |
| Form A | Slurry | Dioxane | Room temp. | 2 | Form H |
| Form A | Slurry | THF | Room temp. | 2 | Form I |
| Form A | Slurry | Acetone | Room temp. | 2 | Form G |
| Form A | Slurry | Toluene/MeCN 3:1 | Room temp. | 2 | Form J |
| Form A | Slurry | Cyclohexane/EtOH 4:1 | Room temp. | 2 | Form D |
| Form D | Slurry | cyclohexane | Room temp. | 2 | Analyzed by FT-Raman |
| Form A | Slurry | cyclohexane | Room temp. | 2 | Analyzed by FT-Raman |
| Form A | Slurry | n-octane | 110 | 1 | Analyzed by FT-Raman |
| Form A | Slurry | Cyclohexane/EtOH 4:1 | Room temp. | 1 | Form D |
| Form A | Slurry | Cyclohexane/EtOH 4:1 | Room temp. | 1 | Form D |
| Form D | Slurry | n-octane | Room temp.–110 | 3 | Analyzed by FT-Raman; amorphous |
| Form D | Slurry | mesitylene | Room temp.–110 | 3 | Analyzed by FT-Raman |
| Form C | Slurry | water | 1 | 2 | Analyzed by FT-Raman |
| Form C | Slurry | Acetone/water 1:1 | 1-room temp. | 3 | Analyzed by FT-Raman |
| Form C | Slurry | n-octane | 110 | 3 | Analyzed by FT-Raman |
| Form H | Slurry | n-octane | 110 | 3 | Amorphous |
| Form G | Slurry | n-octane | 80 | 3 | Analyzed by FT-Raman |
| Form J | Slurry | n-octane | 110 | 3 | Amorphous |
| Form D | Slurry | n-octane/EtOH 36:1 | 80 | 3 | Form E |
| Form D | Slurry | water | 80 | 1 | Analyzed by FT-Raman |
| Form A | Slurry | Cyclohexane/EtOH 4:1 | Room temp. | 2 | Form D |
| Form A | Slurry | Acetone | Room temp. | 2 | Form G |
| Form A | Slurry | Water | Room temp. | 1 | Analyzed by FT-Raman |
| Form D | Slurry | n-octane/EtOH 36:1 | 80 | 3 | Analyzed by FT-Raman |
| Form D | Slurry | n-octane/EtOH 18:1 | 80 | 3 | Analyzed by FT-Raman |

TABLE 4

Precipitation results

| Starting material | Solvent[1] | Temperature (° C.) | Time stirred (hours) | Outcome/remarks |
|---|---|---|---|---|
| Form A | Cyclohexane/EtOH 1:1; 1x cyclohexane | 70 | 2 | Form B |
| Form A | n-octane/EtOH 4:1; 1x n-octane | 75 | 1 | Form D |

[1]First solvent or solvent mixture: solvent; second solvent: antisolvent. "1x" for example means that the compound is precipitated by adding the same volume of antisolvent to the solution.

For the drying/water vapor adsorption experiments, Form D is dried under nitrogen for three days to result in Form E.

TABLE 5a

Drying/water vapor adsorption

| Starting material | Process | Solvent | Condition | Time (days) | Outcome/remarks |
|---|---|---|---|---|---|
| Form D | Water vapor adsorption | N/A | 81% RH; nitrogen | 17 | Analyzed by FT-Raman |
| Form G | Water vapor adsorption | N/A | 81% RH; nitrogen | 25 | Analyzed by FT-Raman |
| Form A | Water vapor adsorption | N/A | 81% RH; nitrogen | 38 | Analyzed by FT-Raman; 4% water and 2% ethyl acetate |
| Form D | Drying | N/A | nitrogen | 3 | Form E |
| Form G | Drying | N/A | nitrogen | 2 | Analyzed by FT-Raman |
| Form G | Drying | N/A | vacuum | 34 | Analyzed by FT-Raman |

TABLE 5b

Evaporation results

| Starting material | Process | Solvent | Condition | Time (days) | Outcome/remarks |
|---|---|---|---|---|---|
| Form A | Evaporation | EtOH/water 19:1 | Nitrogen, room temp. | 5 | Analyzed by FT-Raman; crystallized after storage in refrigerator for 20 days |

TABLE 5b-continued

Evaporation results

| Starting material | Process | Solvent | Condition | Time (days) | Outcome/ remarks |
|---|---|---|---|---|---|
| Form A | Evaporation | 0.1M TRIS-buffer | Nitrogen, room temp. | 12 | Form C, evaporation to 40% of initial volume |
| Form A | Evaporation | 0.05M TRIS-buffer, pH 7.4 | Nitrogen, room temp. | 16 | Form K, evaporation to 15% of initial volume |

Example 1

Figure 3:
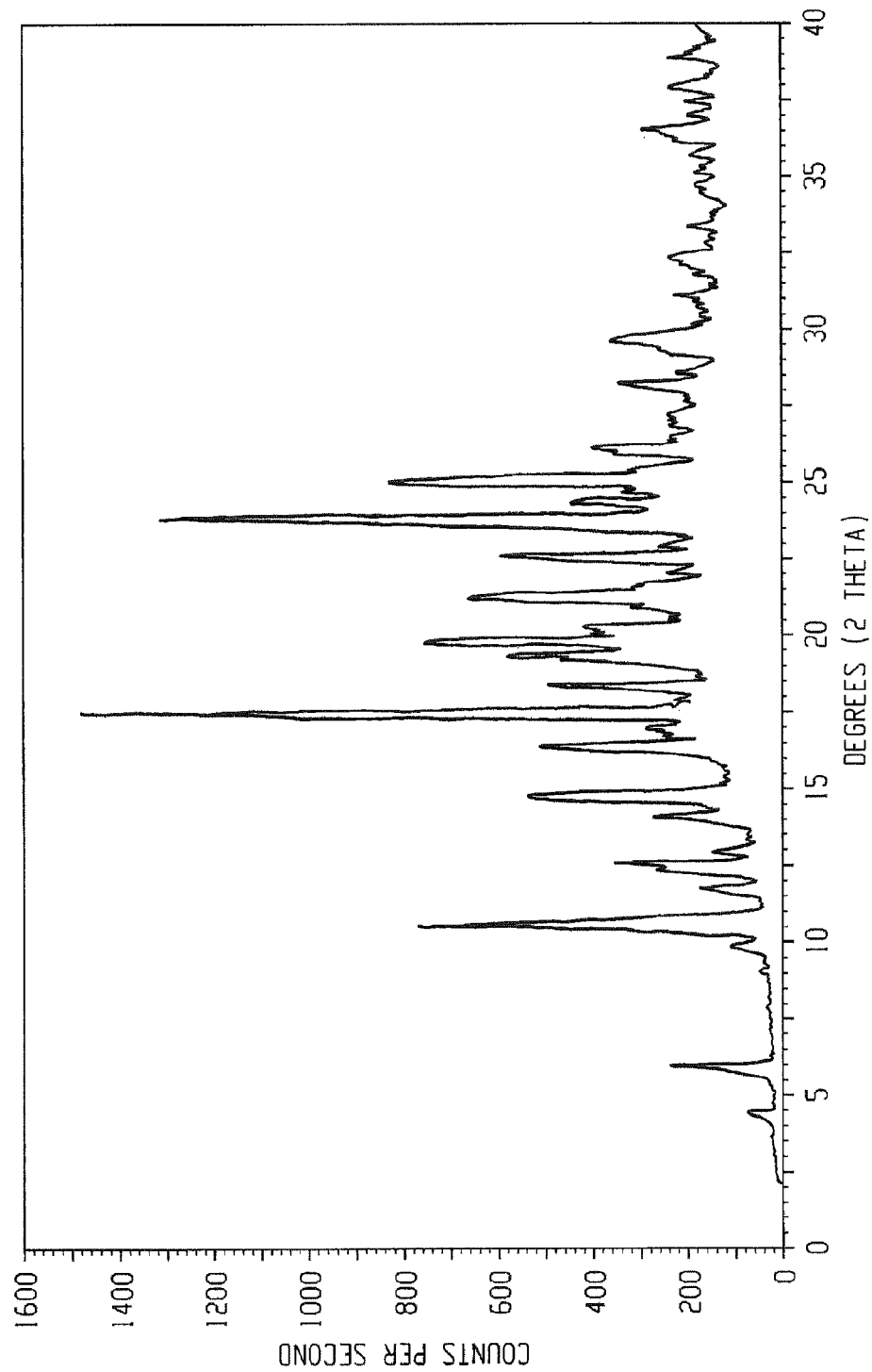
FIG. 3 illustrates XRPD pattern of colchicine Form B.
Figure 4:
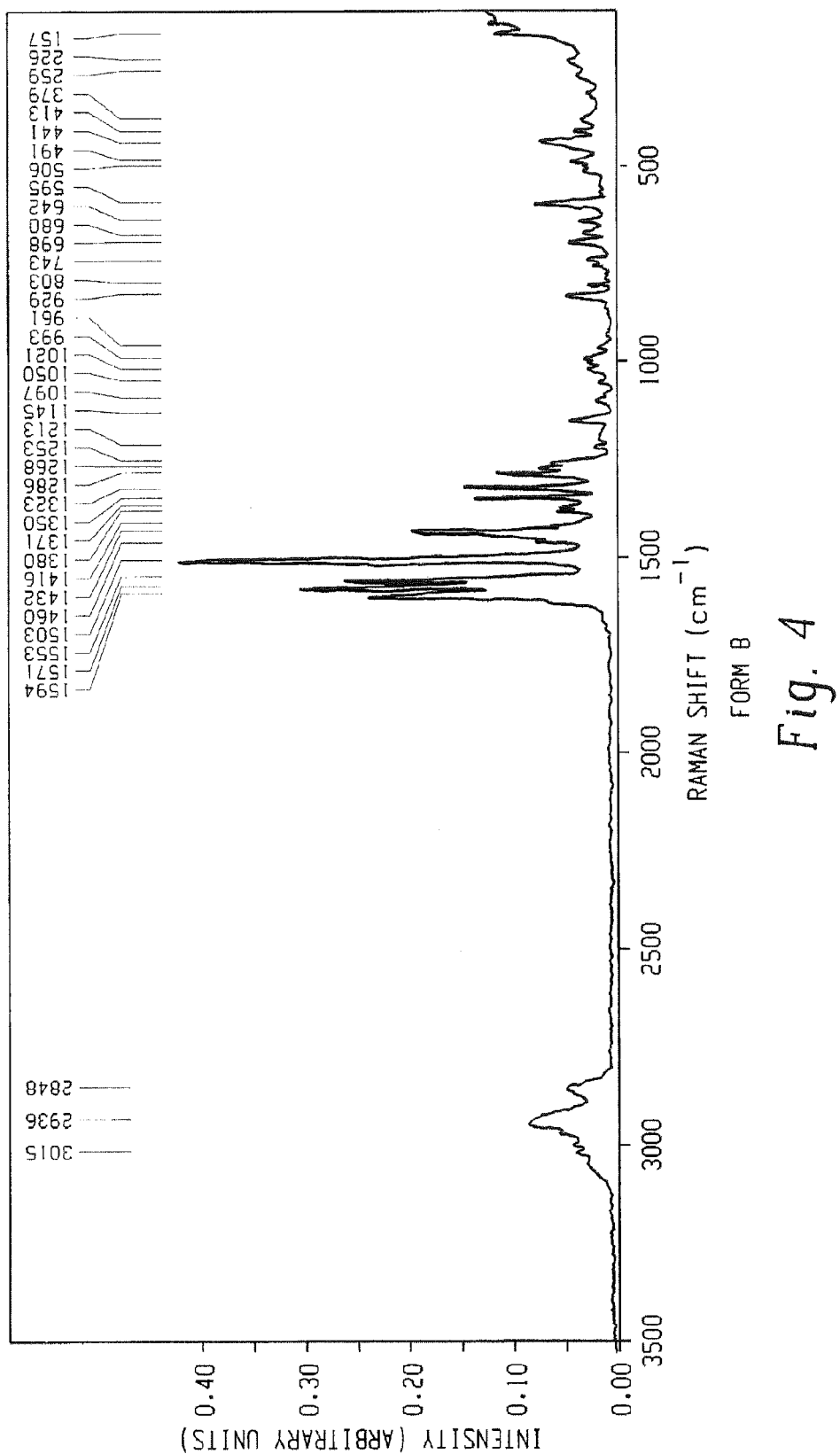
FIG. 4 illustrates a FT-Raman spectrum of colchicine Form B.

Preparation of Colchicine Form B 311 milligrams (mg) of colchicine Form A is dissolved in 9 milliliters (ml) 1:9 (v:v) EtOH/cyclohexane at 70° C. An additional 9 ml of cyclohexane is added and the suspension is stirred for 1 hour at 70° C. The resulting solids (88 mg) are filtered, air-dried and analyzed by FT-Raman, XRPD, and TG-FTIR. FIG. 3 illustrates an XRPD pattern of Form B with a peak listing provided in Table 6 below. FIG. 4 illustrates a FT-Raman spectrum and a peak listing is provided in Table 6. The results indicate Form B is a cyclohexane solvate containing 5.6% solvent.

TABLE 6

XRPD and FT-Raman peak table of colchicine Form B

| XRPD peaks | | FT-Raman peaks |
|---|---|---|
| 2θ [°] | Intensity [%] | (cm⁻¹) |
| 4.28 | 5 | 3015 |
| 5.79 | 16 | 2995 |
| 9.83 | 8 | 2965 |
| 10.50 | 51 | 2936 |
| 11.68 | 12 | 2848 |
| 12.33 | 17 | 1594 |
| 12.48 | 25 | 1571 |
| 12.91 | 10 | 1553 |
| 14.03 | 17 | 1503 |
| 14.73 | 36 | 1460 |
| 16.38 | 36 | 1432 |
| 16.93 | 20 | 1416 |
| 17.47 | 100 | 1380 |
| 18.36 | 32 | 1371 |
| 19.08 | 31 | 1350 |
| 19.33 | 41 | 1323 |
| 19.78 | 52 | 1286 |
| 20.25 | 29 | — |
| 21.27 | 45 | — |
| 22.57 | 38 | — |
| 22.96 | 18 | — |
| 23.86 | 91 | — |
| 24.37 | 32 | — |
| 24.75 | 22 | — |
| 25.11 | 56 | — |
| 25.46 | 22 | — |
| 26.19 | 27 | — |
| 28.27 | 24 | — |
| 28.65 | 15 | — |
| 29.78 | 26 | — |
| 31.20 | 16 | — |
| 32.50 | 17 | — |

TG-FTIR analysis reveals a stepwise weight loss of 5.6% cyclohexane, which is strongest at about 170° C. This is typical for a solvate (4:1 colchicine to solvent 5.0%; 3:1 colchicine to solvent 6.6%). Decomposition is observed above 225° C.

TABLE 7

| Temperature range | Mass loss (%) | Released compound/comment |
|---|---|---|
| 25-225° C. | 5.63 | cyclohexane |
| 225-350° C. | 14.28 | Decomposition |

Example 2

Preparation of Colchicine Form C

Figure 5:
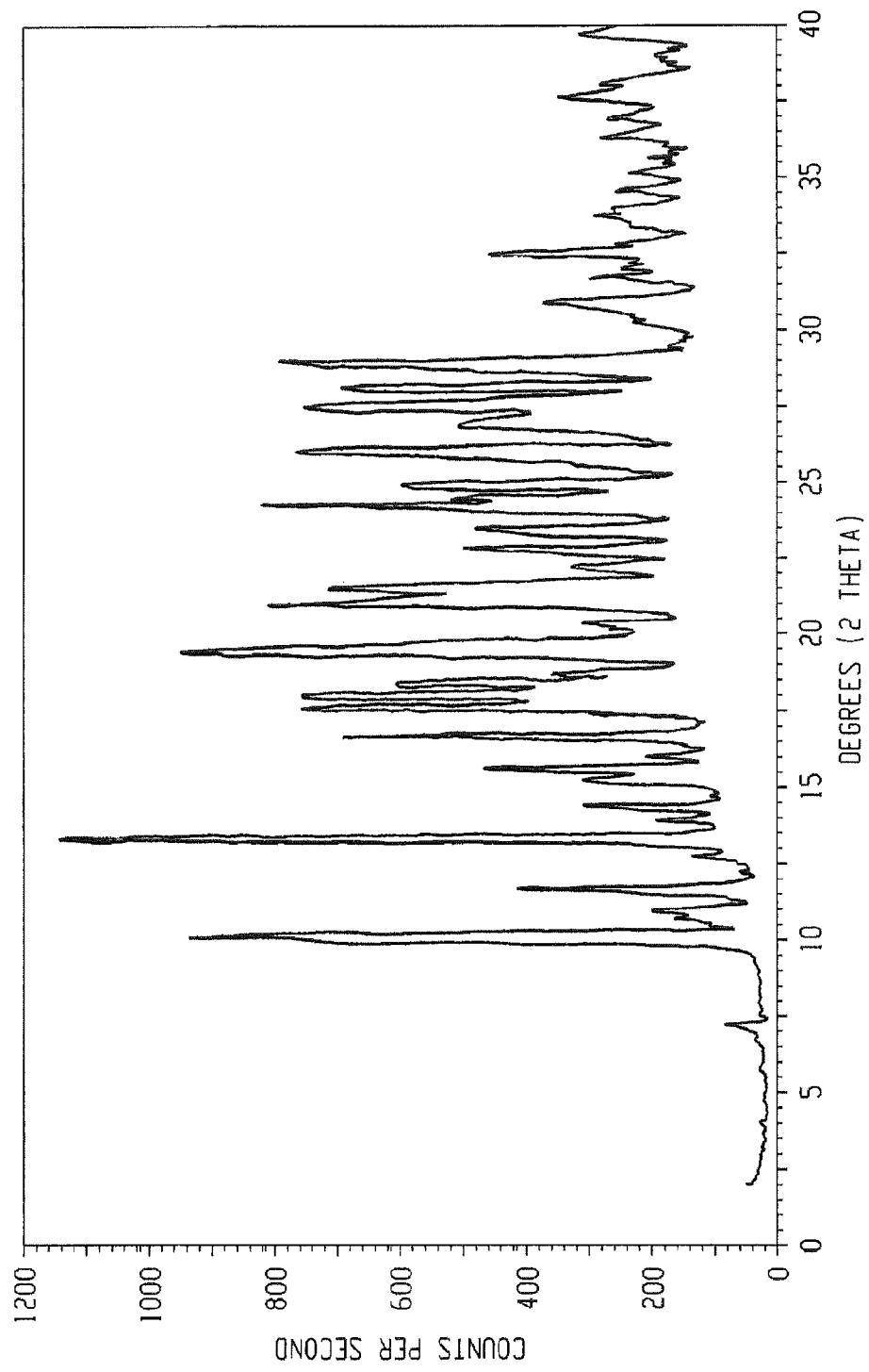
FIG. 5 illustrates XRPD pattern of colchicine Form C.

A. 518 mg of colchicine Form A is suspended in 0.5 ml water and stirred at room temperature. After one day a very viscous suspension is formed. An additional ml of water is added and the suspension is stirred at room temperature for 1 day. The material is stored at room temperature and 75% relative humidity (RH) for three weeks. The resulting solids are analyzed by FT-Raman, XRPD, TG-FTIR, and DVS. FIG. 5 illustrates an XRPD pattern of Form C with a peak listing provided in Table 8 below. FIG. 6 illustrates a FT-Raman spectrum and a peak listing is provided in Table 8. The results indicate Form C is a hydrate containing 7.6% water.

B. 1.9 grams (g) colchicine Form A is suspended in 5 ml water and seeded with the material from Example 2A. The suspension is stirred at room temperature for a day, filtered and dried at ambient conditions. The resulting solids are analyzed by FT-Raman and differential scanning calorimetry (DSC).

TABLE 8

XRPD and FT-Raman peak table of colchicine Form C

| XRPD peaks | | FT-Raman peaks |
|---|---|---|
| 2θ [°] | Intensity [%] | (cm⁻¹) |
| 7.19 | 7 | 3041 |
| 10.11 | 80 | 3019 |
| 10.95 | 18 | 3000 |
| 11.69 | 36 | 2981 |
| 12.76 | 10 | 2930 |
| 13.35 | 100 | 2865 |
| 13.93 | 16 | 2846 |
| 14.32 | 23 | 1597 |
| 15.23 | 27 | 1587 |
| 15.55 | 40 | 1565 |
| 15.97 | 18 | 1544 |
| 16.61 | 59 | 1500 |
| 17.58 | 67 | 1434 |
| 17.93 | 62 | 1366 |
| 18.34 | 56 | 1350 |
| 18.66 | 31 | 1323 |
| 19.44 | 75 | 1285 |
| 20.30 | 25 | 1254 |
| 21.00 | 72 | — |
| 21.42 | 60 | — |
| 22.18 | 28 | — |
| 22.74 | 45 | — |
| 23.46 | 39 | — |
| 24.23 | 74 | — |
| 24.48 | 43 | — |
| 24.91 | 52 | — |
| 25.96 | 66 | — |
| 26.87 | 44 | — |
| 27.38 | 64 | — |
| 27.57 | 51 | — |

TABLE 8-continued

XRPD and FT-Raman peak table of colchicine Form C

| XRPD peaks | | FT-Raman peaks |
|---|---|---|
| 2θ [°] | Intensity [%] | (cm$^{-1}$) |
| 28.05 | 59 | — |
| 28.87 | 70 | — |
| 30.88 | 33 | — |
| 31.66 | 27 | — |
| 32.43 | 41 | — |
| 33.47 | 21 | — |
| 34.55 | 23 | — |

TG-FTIR analysis reveals a stepwise weight loss of 7.6% water, which is strongest at about 140° C. This is typical for a hydrate (sesquihydrate 6.3%). Decomposition is observed above 220° C.

TABLE 9

| Temperature range | Mass loss (%) | Released compound/comment |
|---|---|---|
| 25-220° C. | 7.58 | water |
| 220-350° C. | 19.25 | Decomposition |

Figure 7A:
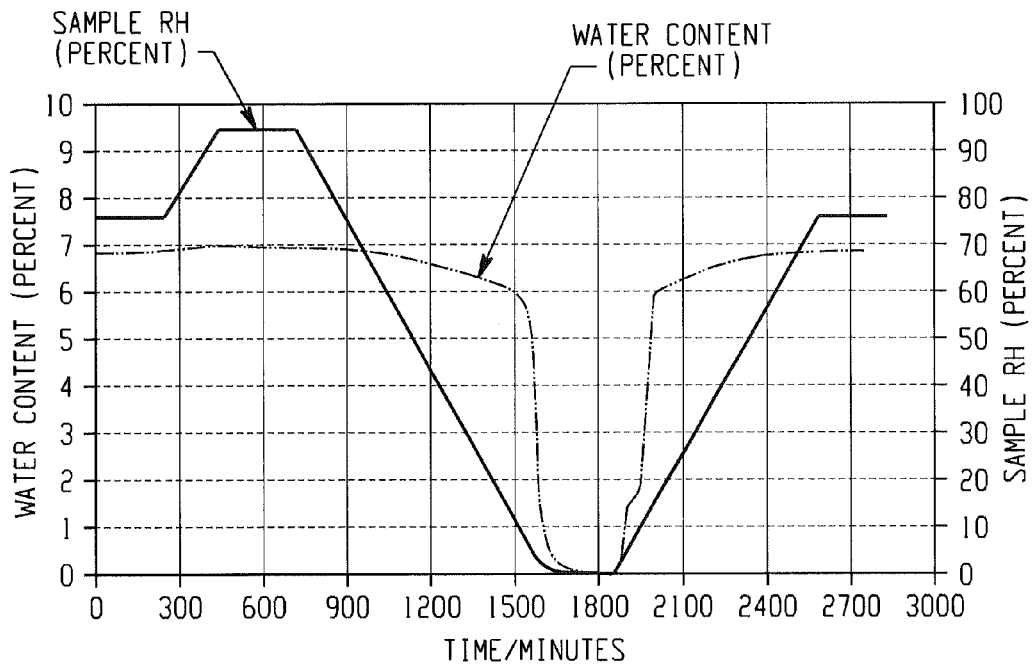
FIG. 7A illustrates a DVS curve of colchicine Form C relative humidity/mass change versus time.
Figure 7B:
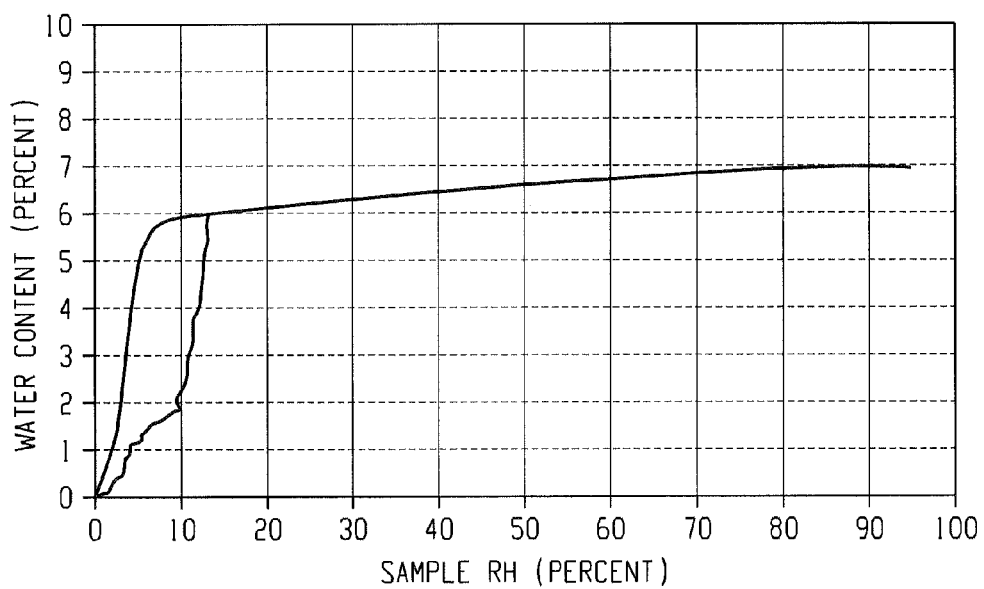
FIG. 7B illustrates a DVS curve of colchicine Form C mass change versus relative humidity).

Form C has a melting peak of 115° C. by DSC analysis. DVS analysis results are provided in FIGS. 7A and 7B. A standard scanning rate of 5% RH change per hour is used in the measurement. Below 10% RH a strong loss of water is observed. At 0% RH the sample likely contains no water. Above a few % RH a strong and stepwise water uptake is observed suggesting the product at 0% RH is highly hygroscopic. The plateau observed at about 7.5% RH may suggest the presence of another hydrate Example 3

Preparation of Colchicine Form D

A. A solubility study is run to determine the solubility of colchicine Form A in 1:1 (v:v) cyclohexane/ethanol at room temperature. After 1 day at room temperature, a precipitate is observed and isolated. 461 mg of colchicine Form A is suspended in 2.0 ml 4:1 (v/v) cyclohexane/ethanol and stirred at room temperature for 1 day. The suspension is seeded with the precipitate from the solubility study and stirred 1 day at room temperature, filtered, and air dried for about 3 minutes at room temperature (293 mg). The resulting solids are analyzed by FT-Raman, and TG-FTIR. The results indicate Form D is an ethanol solvate containing about 10.2% ethanol.

B. Suspended 1.02 g of colchicine in 4 ml 4:1 (v/v) cyclohexane/ethanol, seed with material from Example 3A and stirred for 1 day at room temperature. The resulting material is filtered and dried under ambient conditions; the resulting solid is analyzed by FT-Raman and XRPD.

C. Suspended 2 g of colchicine Form A in 8 ml 4:1 (v/v) cyclohexane/ethanol, seed with material from Example 3B and stirred for 2 days at room temperature. The resulting material is filtered and dried under ambient conditions; the resulting solid is analyzed by FT-Raman, TG-FTIR, DSC, and $^1$H-NMR.

Figure 8:
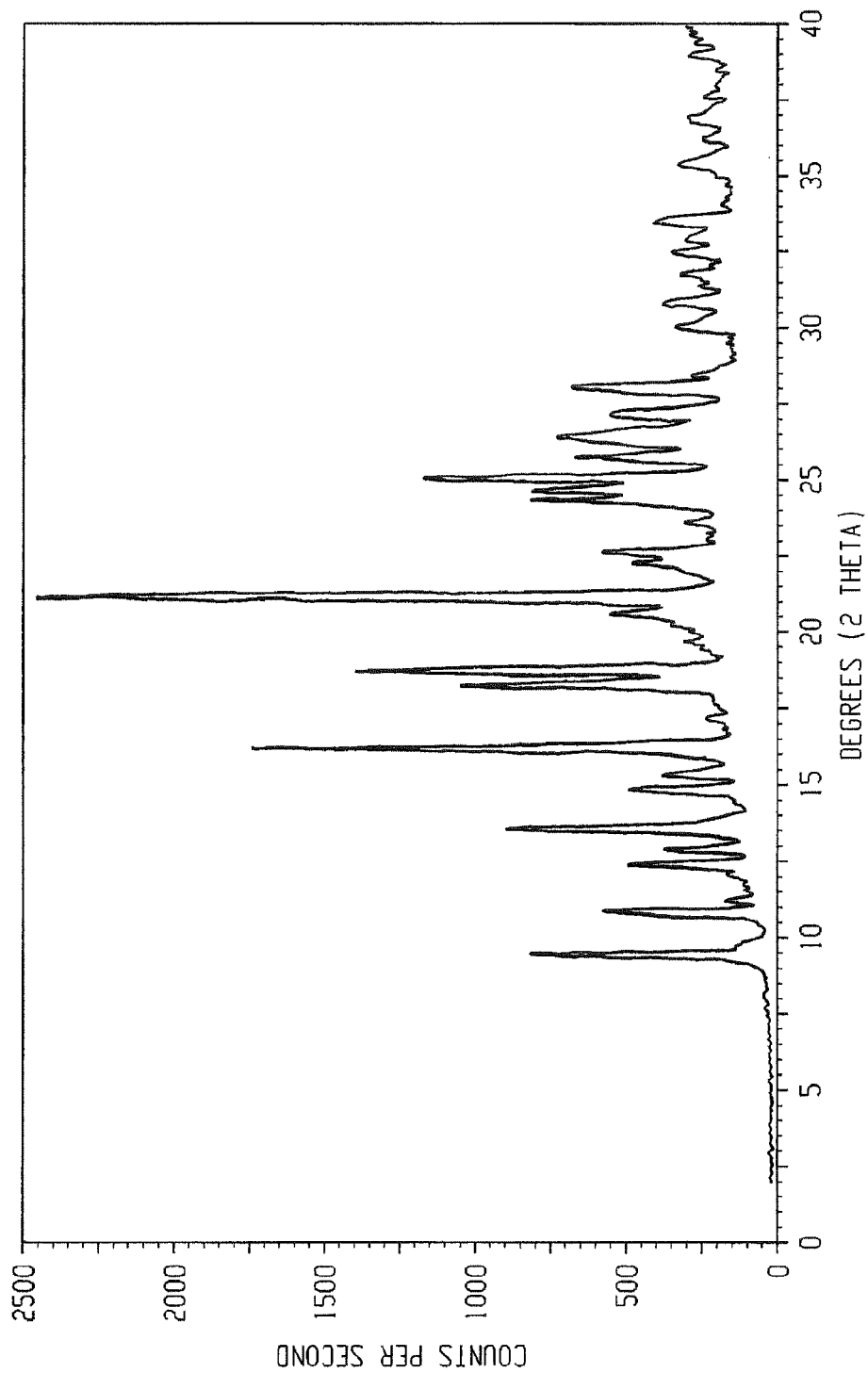
FIG. 8 illustrates XRPD pattern of colchicine Form D.
Figure 9:
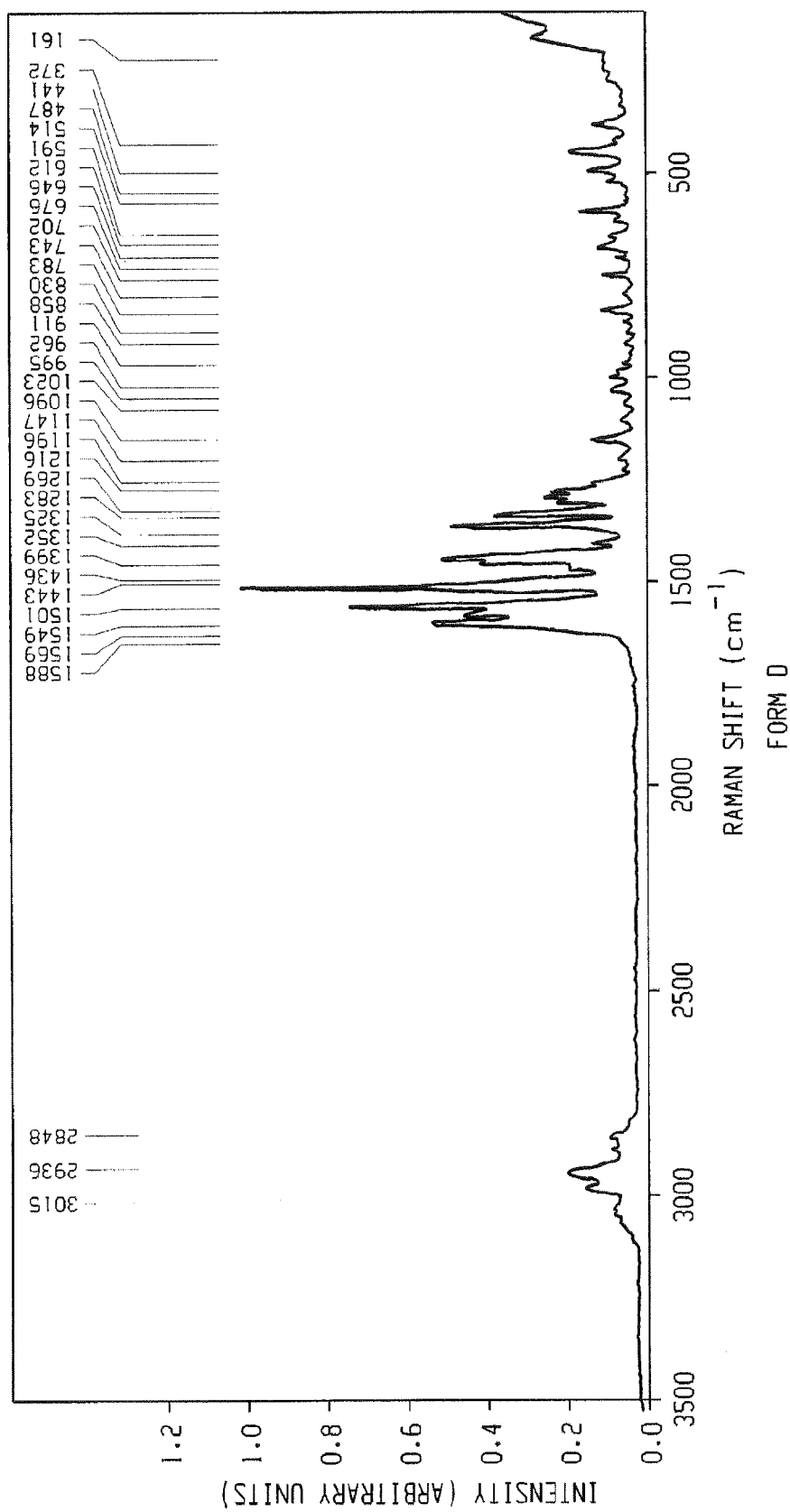
FIG. 9 illustrates a FT-Raman spectrum of colchicine Form D.

FIG. 8 illustrates an XRPD pattern of Form D with a peak listing provided in Table 10 below. FIG. 9 illustrates a FT-Raman spectrum and a peak listing is provided in Table 10.

TABLE 10

XRPD and FT-Raman peak table of colchicine Form D

| XRPD peaks | | FT-Raman peaks |
|---|---|---|
| 2θ [°] | Intensity [%] | (cm$^{-1}$) |
| 9.45 | 31 | 3027 |
| 9.75 | 6 | 3016 |
| 10.88 | 24 | 2968 |
| 11.21 | 7 | 2933 |
| 12.44 | 20 | 2840 |
| 12.97 | 16 | 1588 |
| 13.63 | 37 | 1569 |
| 14.91 | 20 | 1549 |
| 15.46 | 16 | 1501 |
| 16.26 | 70 | 1443 |
| 17.29 | 10 | 1436 |
| 18.31 | 45 | 1399 |
| 18.76 | 57 | 1352 |
| 19.66 | 13 | 1325 |
| 20.62 | 23 | 1283 |
| 21.16 | 100 | 1269 |
| 22.25 | 20 | — |
| 22.58 | 25 | — |
| 23.62 | 12 | — |
| 24.32 | 36 | — |
| 24.65 | 31 | — |
| 25.10 | 49 | — |
| 25.78 | 28 | — |
| 26.45 | 31 | — |
| 26.65 | 23 | — |
| 27.26 | 22 | — |
| 28.14 | 30 | — |
| 28.48 | 12 | — |
| 30.10 | 14 | — |
| 30.91 | 16 | — |
| 31.77 | 14 | — |
| 32.50 | 14 | — |
| 33.02 | 13 | — |
| 33.52 | 18 | — |

TG-FTIR analysis reveals a stepwise weight loss of 10.2% ethanol, which is strongest at about 130° C. This is typical for a solvate (monosolvate 10.3%). Decomposition is observed above 270° C.

TABLE 11

| Temperature range | Mass loss (%) | Released compound/comment |
|---|---|---|
| 25-270° C. | 10.16 | ethanol |
| 270-350° C. | 17.65 | Decomposition |

Under DSC analysis, a melting peak with a shoulder is observed at 95° C. and a weak endothermic event at 62° C. Under $^1$H-NMR analysis in CDCl$_3$ 0.9 mol equivalent of ethanol is observed.

Example 4

Preparation of Colchicine Form E

Figure 10:
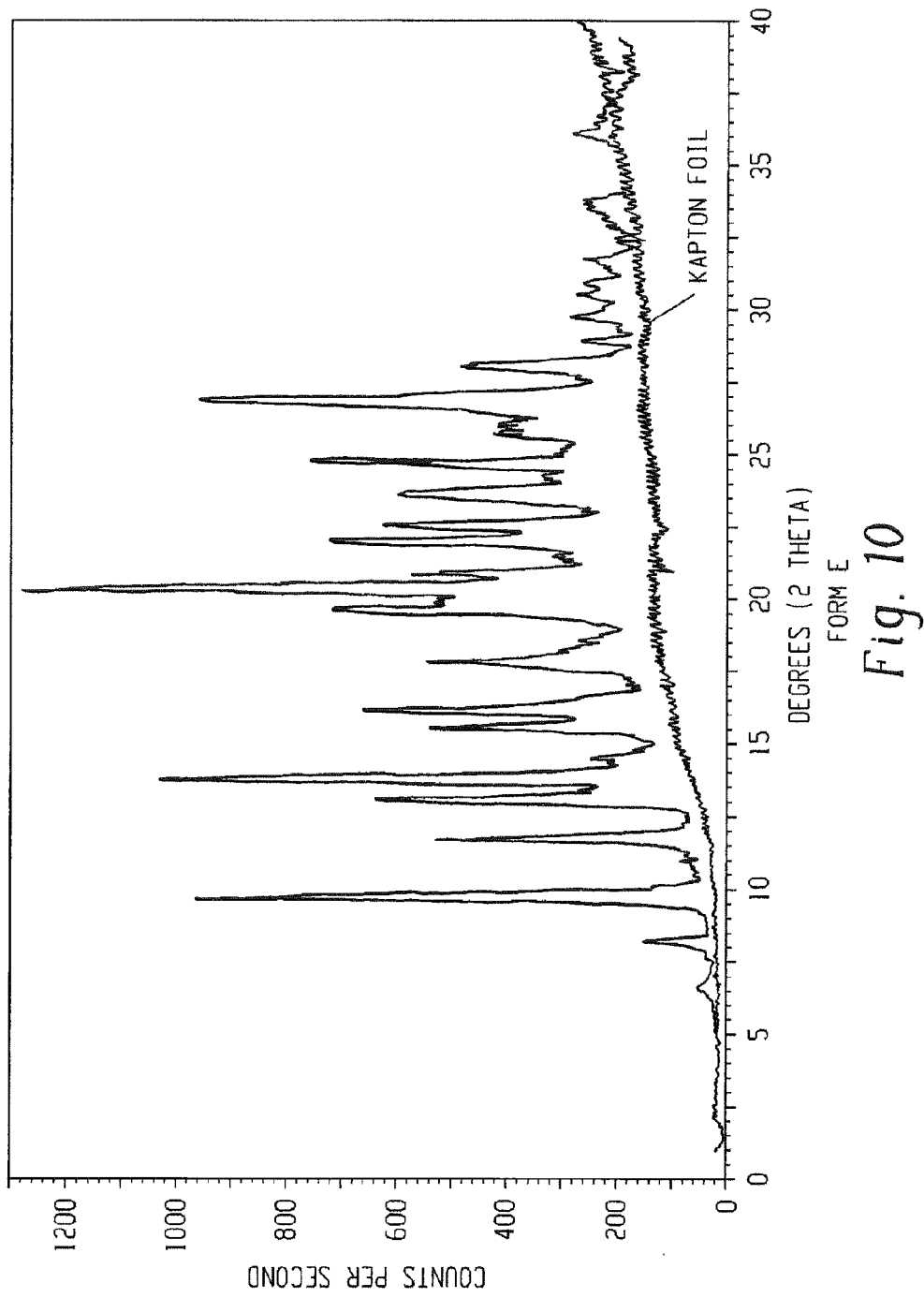
FIG. 10 illustrates XRPD pattern of colchicine Form E.
Figure 11:
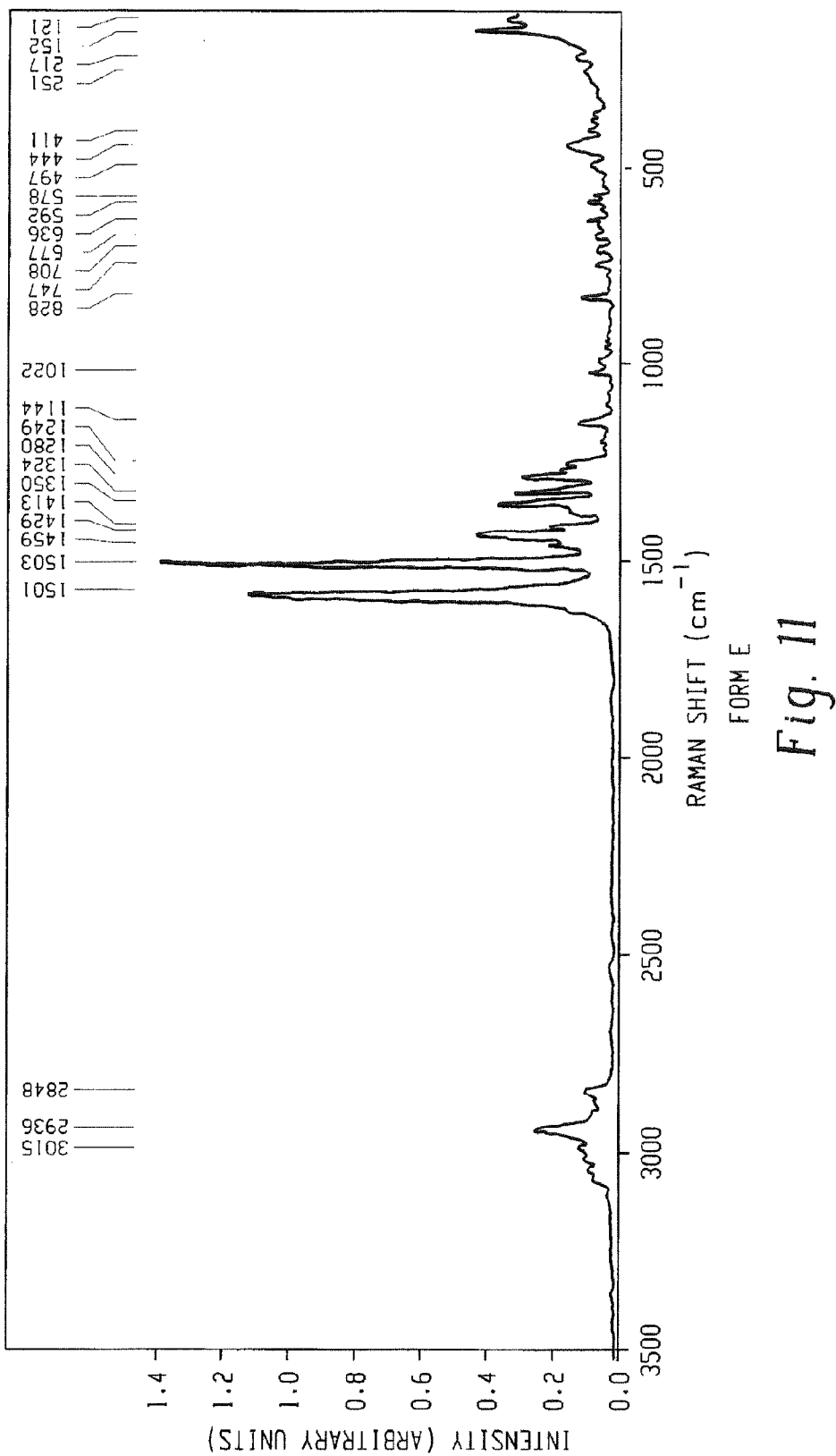
FIG. 11 illustrates a FT-Raman spectrum of colchicine Form E.

A. 280 mg of colchicine Form D obtained according to Example 3B is suspended in 3.0 ml 36:1 (v/v) n-octane/ethanol. The mixture is slowly heated to 80° C. to form a slightly yellow suspension that is stirred at 80° C. for 2 days. The suspension is hot filtered and dried under nitrogen for 1 day at room temperature. The resulting solids are analyzed by FT-Raman, XRPD, and TG-FTIR. FIG. 10 illustrates an XRPD pattern of Form E with a peak listing provided in Table 12 below. FIG. 11 illustrates a FT-Raman spectrum and a peak listing is provided in Table 12. The results indicate Form E is likely an ansolvate containing about 2.1% n-octane or 2.3% water depending upon preparation.

TABLE 12

XRPD and FT-Raman peak table of colchicine Form E

| XRPD peaks | | FT-Raman peaks |
|---|---|---|
| 2θ [°] | Intensity [%] | (cm⁻¹) |
| 6.61 | 4 | 2984 |
| 8.16 | 12 | 2933 |
| 9.79 | 75 | 2836 |
| 11.76 | 41 | 1577 |
| 13.13 | 48 | 1503 |
| 13.81 | 81 | 1459 |
| 15.60 | 43 | 1429 |
| 16.16 | 50 | 1413 |
| 17.79 | 42 | 1350 |
| 19.64 | 52 | 1324 |
| 20.36 | 100 | 1280 |
| 20.88 | 41 | 1249 |
| 22.00 | 55 | — |
| 22.59 | 49 | — |
| 23.67 | 45 | — |
| 24.75 | 57 | — |
| 25.71 | 31 | — |
| 26.90 | 73 | — |
| 28.00 | 38 | — |
| 28.89 | 20 | — |
| 29.72 | 22 | — |

TG-FTIR analysis reveals about 2% loosely bound solvent indicating Form E is likely an ansolvate. The solvent is likely residual solvent from synthesis. Decomposition is observed above 250° C.

TABLE 13

| Temperature range | Mass loss (%) | Released compound/comment |
|---|---|---|
| 25-250° C. | 2.12 | n-octane |
| 250-350° C. | 9.77 | Decomposition |

B. 301 mg of colchicine Form D obtained according to Example 3C is dried under nitrogen for 3 days at room temperature. The resulting material is analyzed by FT-Raman, XRPD, and TG-FTIR.
TG-FTIR analysis reveals about 2% loosely bound solvent indicating Form E is likely an ansolvate. The solvent is likely residual solvent from synthesis and water may be due to open handling of the sample. Decomposition is observed above 250° C.

TABLE 14

| Temperature range | Mass loss (%) | Released compound/comment |
|---|---|---|
| 25-250° C. | 2.28 | Water; small amt cyclohexane |
| 250-350° C. | 9.60 | Decomposition |

Example 5

Figure 12:
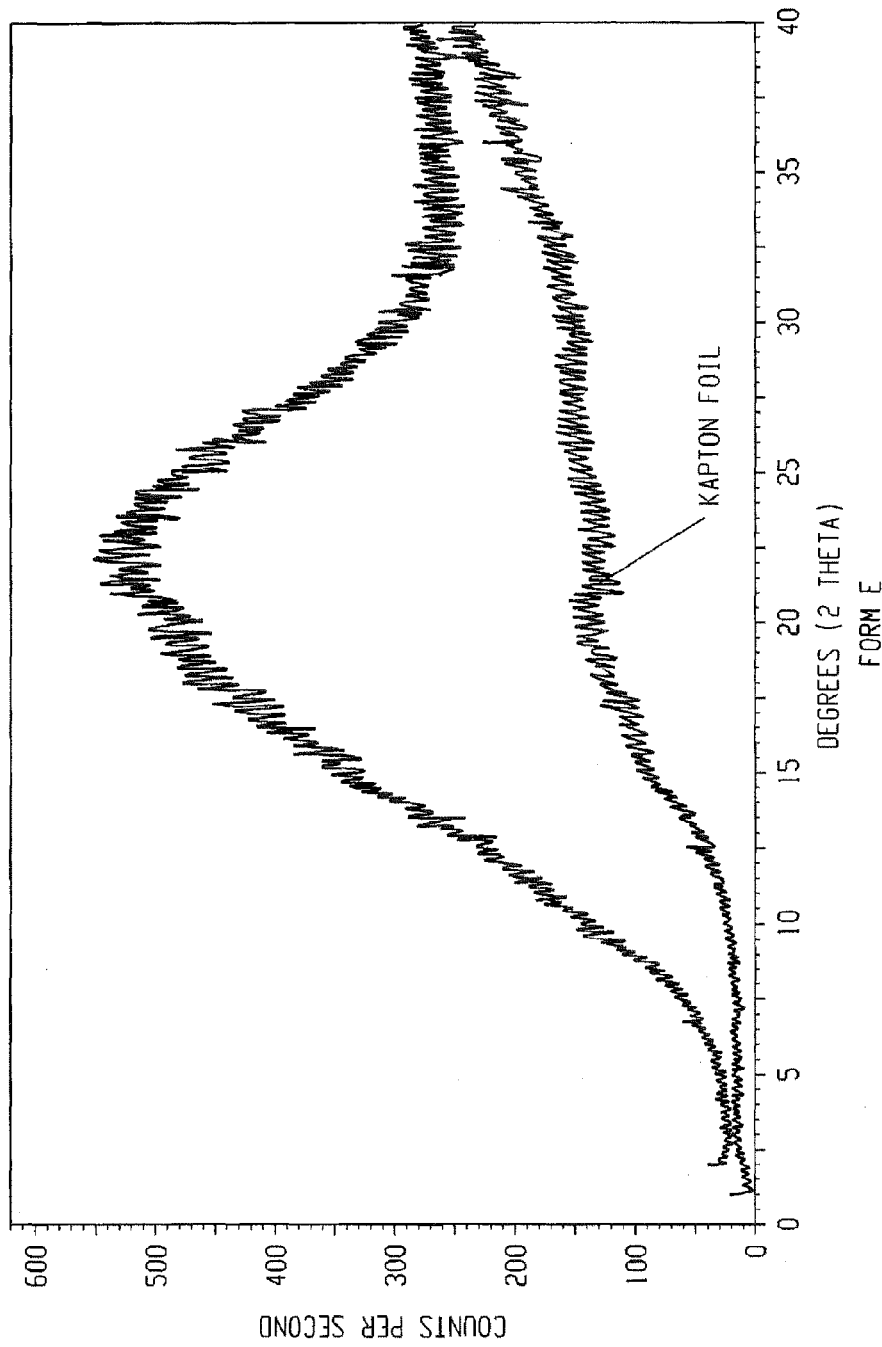
FIG. 12 illustrates XRPD pattern of colchicine Form F.
Figure 13:
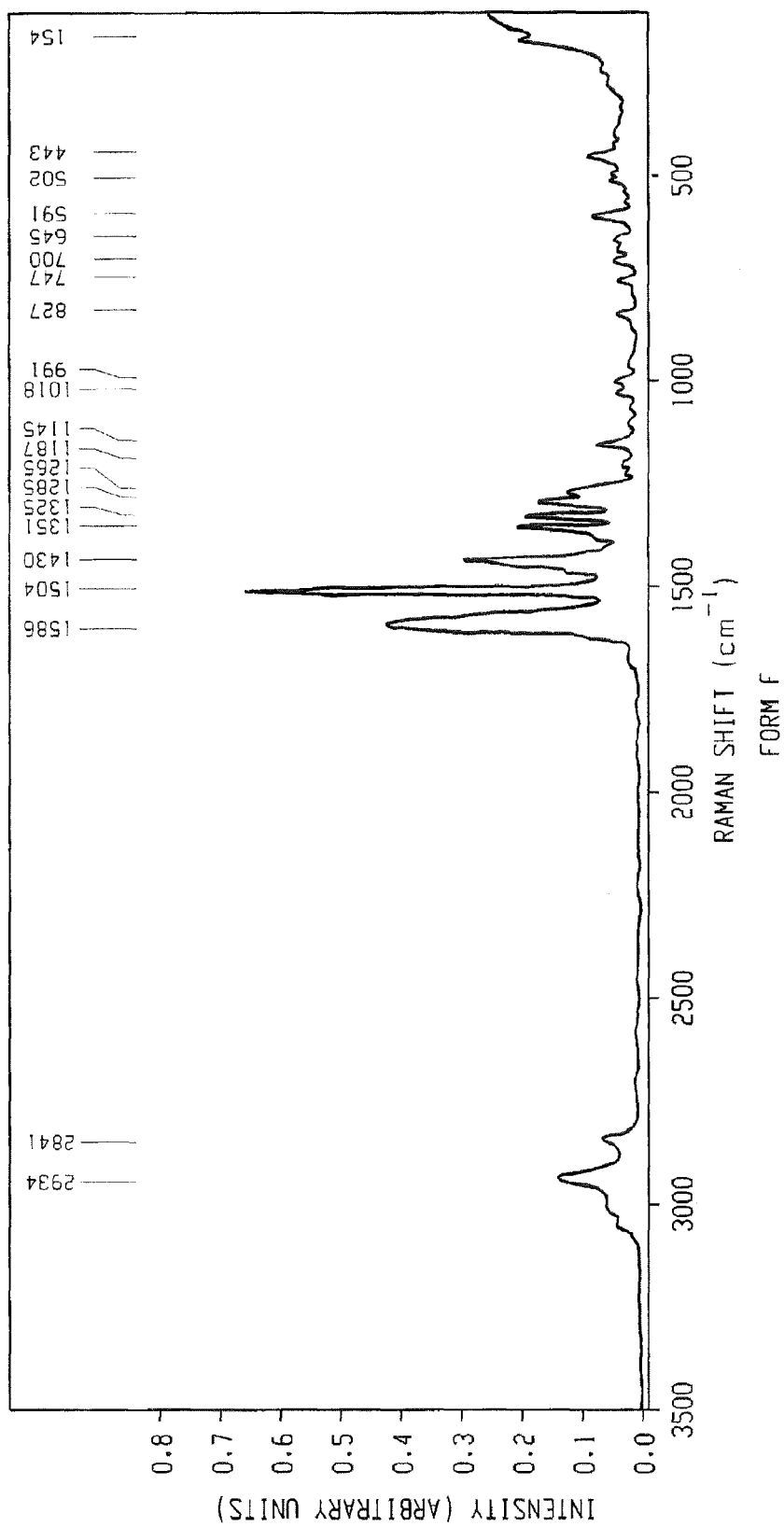
FIG. 13 illustrates a FT-Raman spectrum of colchicine Form F.

Preparation of Colchicine Form F, Non-Crystalline 1.9 grams of Form A is suspended in 5 ml water, seeded, stirred for 1 day at room temperature and isolated. 485 mg of the isolated material is dried under nitrogen for 3 days at room temperature and then heated under nitrogen to 160° C. for minutes. The non-crystalline material is cooled to room temperature in ten minutes ("melt quenching"). The material is analyzed by FT-Raman, XRPD, TG-FTIR and DSC indicating an amorphous form. FIG. 12 illustrates an XRPD pattern of Form F. FIG. 13 illustrates a FT-Raman spectrum and a peak listing is provided in Table 15.

TABLE 15

FT-Raman peak table of colchicine Form F
FT-Raman peaks (cm⁻¹)

| 2934 |
| 2841 |
| 1586 |
| 1504 |
| 1430 |
| 1351 |
| 1323 |
| 1285 |

TG-FTIR analysis reveals about 1.2% loosely water indicating it is likely derived from open handling of the sample suggesting the Form F is hygroscopic. Decomposition is observed above 280° C.

TABLE 16

| Temperature range | Mass loss (%) | Released compound/comment |
|---|---|---|
| 25-180° C. | 1.21 | Water |
| 180-350° C. | 8.60 | Decomposition |

Analysis by DSC indicates in a first scan, a pronounced $T_g$ at 98° C. and an event at 28° C. which possibly corresponds to a $T_g$ as well. The water observed in TG-FTIR may lower the $T_g$ at the surface of the sample leading to the observation of the $T_g$ at 28° C. An endothermic event is observed at 129° C. possibly corresponding to a melting of a minor crystalline phase. An event observed at 157° C. is thought to be an artifact. A second scan is taken on the same sample after a fast cooling to −50° C. A $T_g$ is observed at 98° C. The absence of other events in the second scan indicates the sample is completely amorphous and homogenous after melting and fast cooling.

Example 5

Preparation of Colchicine Form G

Figure 14:
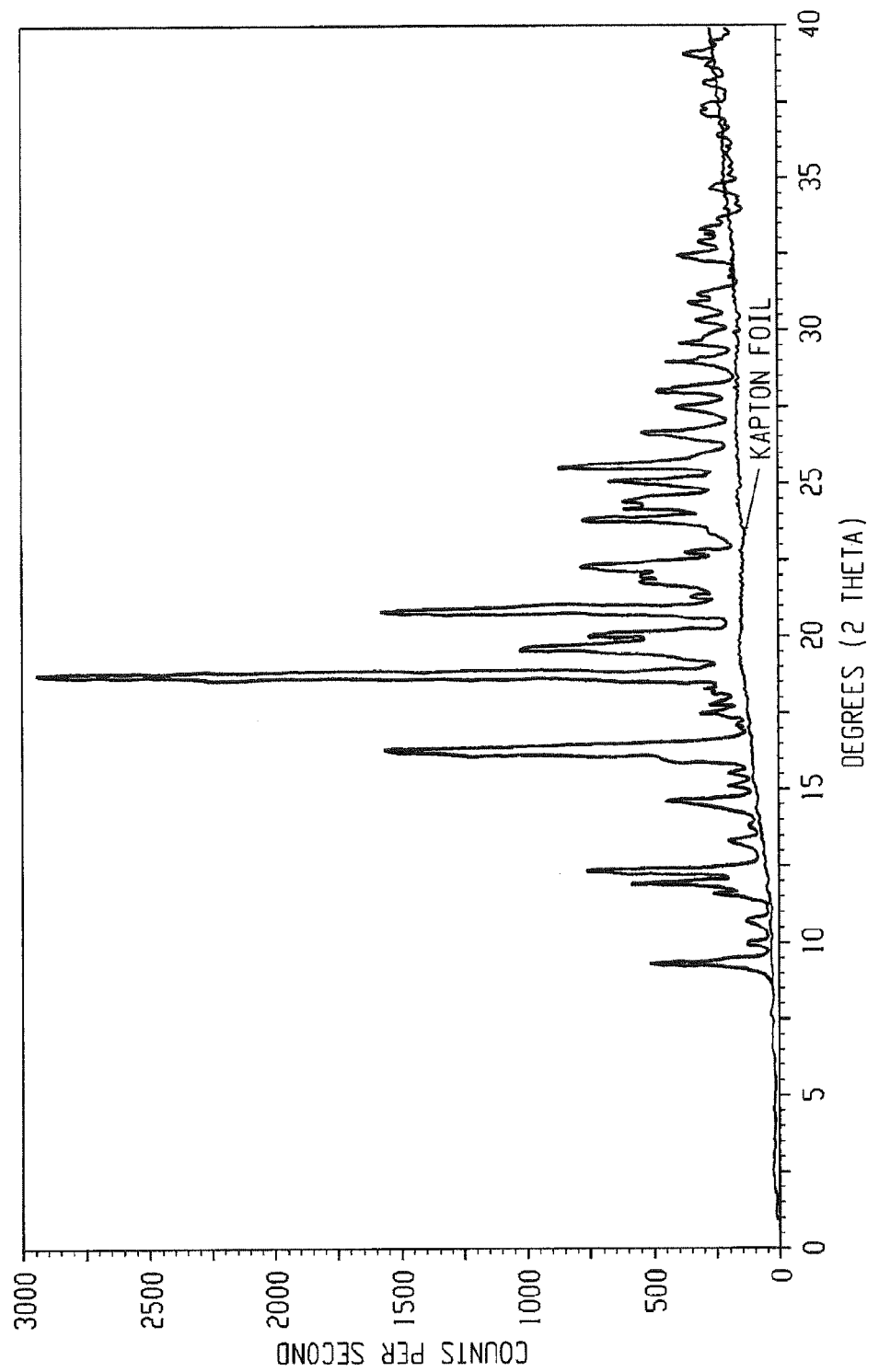
FIG. 14 illustrates XRPD pattern of colchicine Form G.
Figure 15:
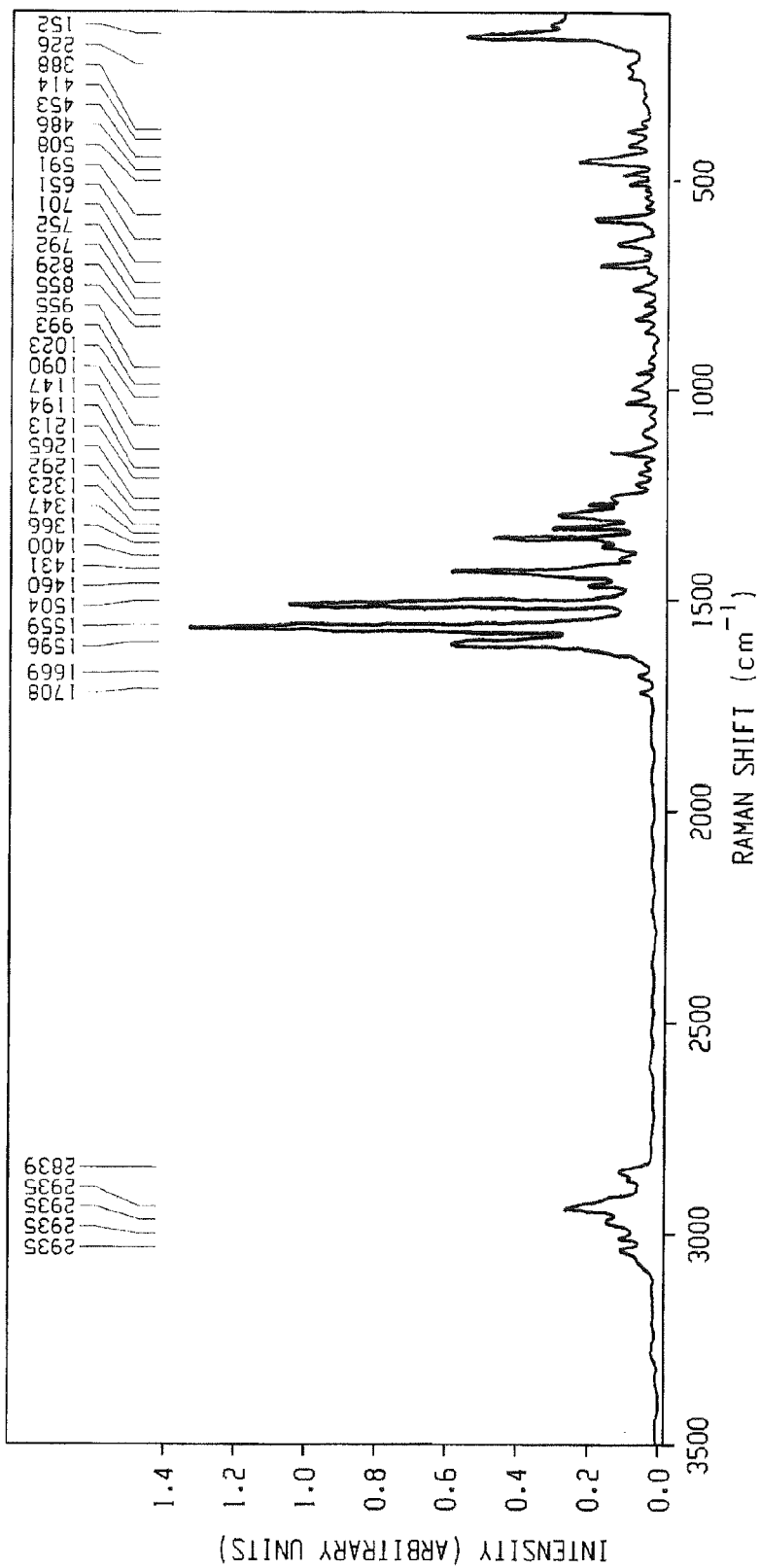
FIG. 15 illustrates a FT-Raman spectrum of colchicine Form G.

A. 500 mg of colchicine Form A is suspended in 1.0 ml acetone and stirred for 1 day at room temperature to form a very viscous suspension. An additional 0.8 ml acetone is added and the suspension is stirred at room temperature for 1 day, filtered and dried at room temperature for 2.5 hours under nitrogen (150 mg). The material is analyzed by FT-Raman and TG-FTIR indicating an acetone solvate containing 18.3% solvent, an amount which may strongly depend upon sample preparation.
B. 2.1 g of colchicine Form A is suspended in 9.0 ml acetone, seeded with material from Example 5A and stirred at room temperature for 2 days. The resulting solid is filtered and dried under ambient conditions. The material is analyzed by FT-Raman, XRPD, DSC, and ¹H-NMR.
FIG. 14 illustrates an XRPD pattern of Form G with a peak listing provided in Table 17 below. FIG. 15 illustrates a FT-Raman spectrum and a peak listing is provided in Table 17.

TABLE 17

XRPD and FT-Raman peak table of colchicine Form G

| XRPD peaks | | FT-Raman peaks |
|---|---|---|
| 2θ [°] | Intensity [%] | (cm$^{-1}$) |
| 9.39 | 18 | 3032 |
| 10.09 | 5 | 2998 |
| 10.83 | 5 | 2963 |
| 11.71 | 9 | 2935 |
| 12.01 | 20 | 2839 |
| 12.41 | 26 | 1708 |
| 13.34 | 5 | 1669 |
| 14.64 | 16 | 1596 |
| 15.12 | 7 | 1559 |
| 15.56 | 7 | 1504 |
| 16.44 | 52 | 1460 |
| 17.58 | 11 | 1431 |
| 18.87 | 100 | 1400 |
| 19.67 | 35 | 1366 |
| 20.03 | 24 | 1347 |
| 20.94 | 53 | 1323 |
| 21.80 | 18 | 1292 |
| 22.28 | 27 | — |
| 22.66 | 12 | — |
| 23.82 | 27 | — |
| 24.44 | 21 | — |
| 25.01 | 23 | — |
| 25.59 | 32 | — |
| 26.68 | 19 | — |
| 27.55 | 14 | — |
| 28.06 | 19 | — |
| 29.01 | 18 | — |
| 29.63 | 13 | — |
| 30.37 | 12 | — |
| 30.92 | 13 | — |
| 31.27 | 11 | — |
| 32.48 | 15 | — |
| 32.87 | 10 | — |
| 33.26 | 11 | — |
| 34.60 | 9 | — |

TG-FTIR analysis reveals a stepwise loss of 18.3% acetone which is strongest around 110° C. The results are typical of a solvate (monosolvate 12.7%; disolvate 22.5%) Decomposition is observed above 200° C.

TABLE 18

| Temperature range | Mass loss (%) | Released compound/comment |
|---|---|---|
| 25-200° C. | 18.32 | acetone |
| 200-350° C. | 11.13 | Decomposition |

TG-FTIR on a completely dry sample shows a solvent content of 8.1%, but the Raman spectrum of the completely dry sample is different from the fresh sample indicating solvent content may vary with sample preparation.

DSC analysis indicates Form G has a melting peak of 87° C. $^1$H-NMR analysis indicates 0.7 mol equivalent of acetone.

Example 6

Preparation of Colchicine Form H

Figure 16:
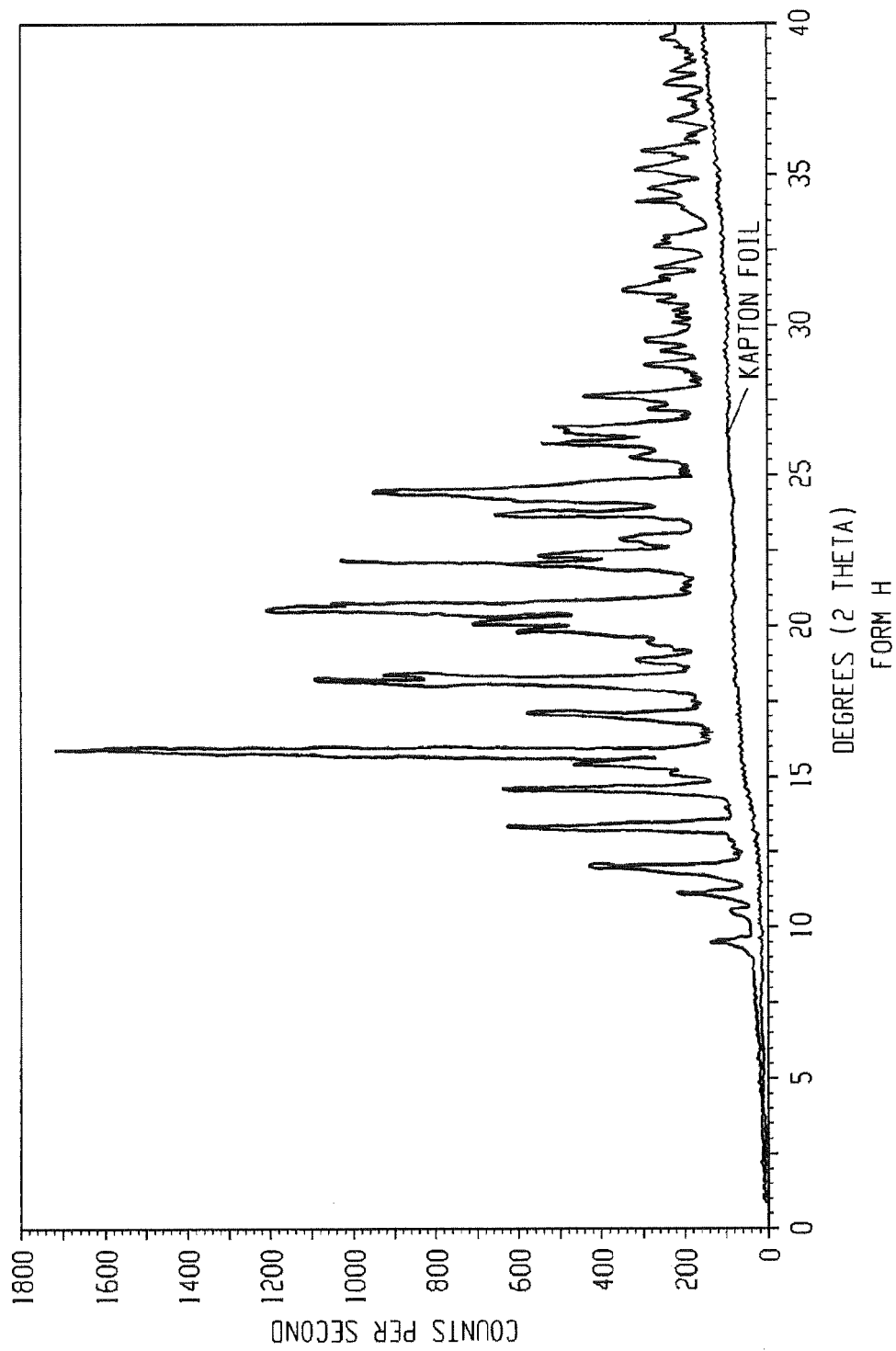
FIG. 16 illustrates XRPD pattern of colchicine Form H.
Figure 17:
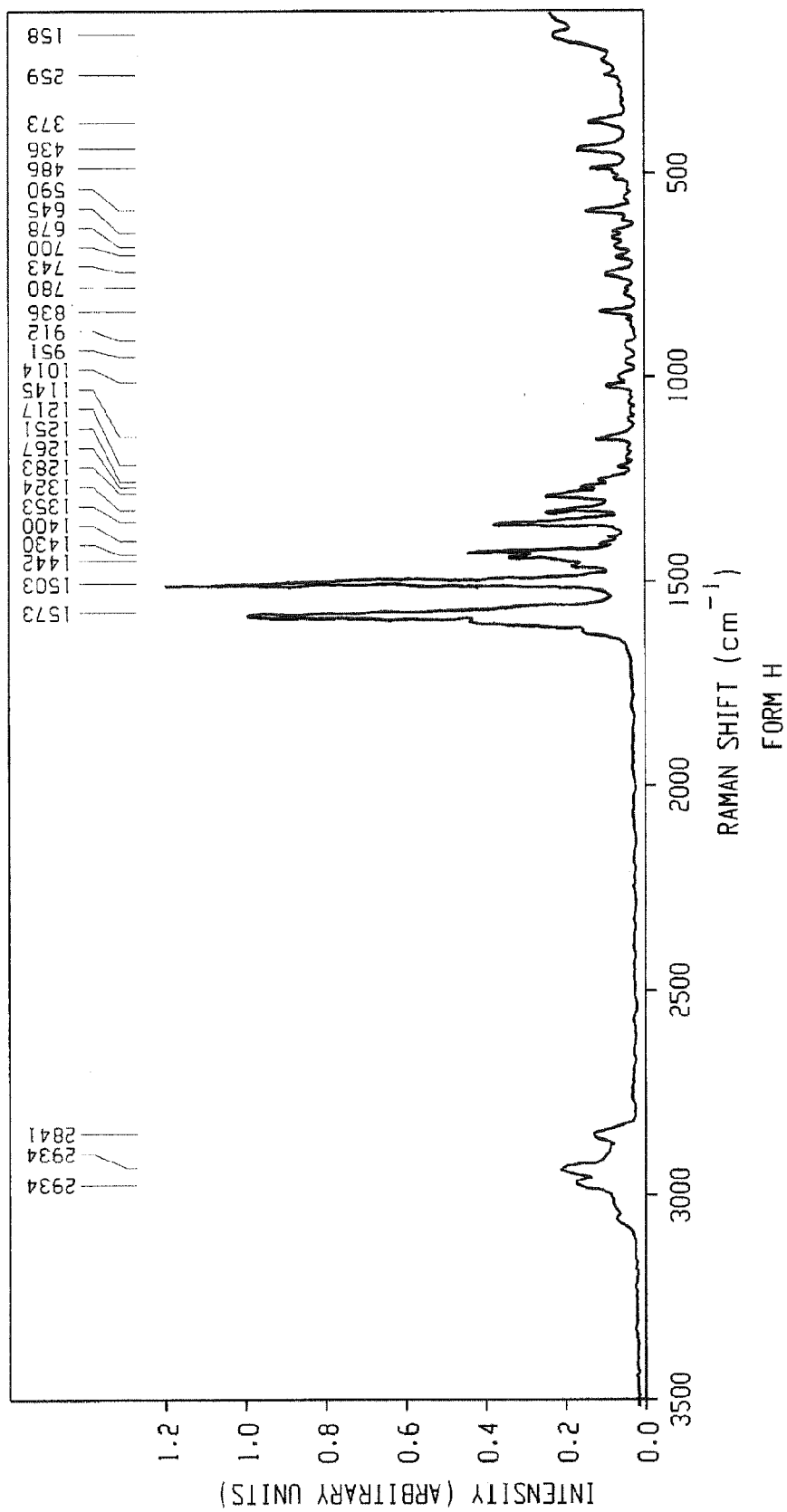
FIG. 17 illustrates a FT-Raman spectrum of colchicine Form H.

A solubility study is run to determine the solubility of colchicine Form A in 1,4-dioxane at room temperature. After 1 day at room temperature, a precipitate is observed and isolated. 471 mg of colchicine Form A is suspended in 1.0 ml 1,4-dioxane and seeded with the precipitate from the solubility study. The suspension is stirred for 2 days at room temperature, filtered, and dried under ambient conditions for several minutes (296 mg). The material is analyzed by FT-Raman, XRPD, and TG-FTIR. FIG. 16 illustrates an XRPD pattern of Form H with a peak listing provided in Table 19 below. FIG. 17 illustrates a FT-Raman spectrum and a peak listing is provided in Table 19. The analysis indicates the material is a dioxane solvate containing about 15.6% solvent.

TABLE 19

XRPD and FT-Raman peak table of colchicine Form H

| XRPD peaks | | FT-Raman peaks |
|---|---|---|
| 2θ [°] | Intensity [%] | (cm$^{-1}$) |
| 9.41 | 8 | 2966 |
| 10.50 | 5 | 2940 |
| 11.10 | 13 | 2846 |
| 12.04 | 25 | 1573 |
| 13.32 | 37 | 1503 |
| 14.57 | 38 | 1442 |
| 15.36 | 27 | 1430 |
| 15.78 | 100 | 1400 |
| 17.04 | 34 | 1353 |
| 18.05 | 65 | 1324 |
| 18.25 | 64 | 1283 |
| 18.92 | 18 | — |
| 19.81 | 37 | — |
| 20.03 | 44 | — |
| 20.35 | 72 | — |
| 20.59 | 71 | — |
| 22.00 | 63 | — |
| 22.33 | 34 | — |
| 22.78 | 23 | — |
| 23.64 | 39 | — |
| 24.13 | 42 | — |
| 24.35 | 58 | — |
| 25.50 | 20 | — |
| 25.95 | 34 | — |
| 26.53 | 31 | — |
| 27.22 | 18 | — |
| 27.56 | 28 | — |
| 28.63 | 18 | — |
| 29.15 | 16 | — |
| 29.48 | 18 | — |
| 30.77 | 15 | — |
| 31.17 | 21 | — |
| 31.95 | 17 | — |
| 32.59 | 17 | — |
| 34.11 | 19 | — |
| 34.48 | 17 | — |

TG-FTIR analysis reveals a stepwise weight loss of 15.6% dioxane which is strongest around 160° C. The results are typical of a solvate (monosolvate 18.1%) Decomposition is observed above 250° C.

TABLE 20

| Temperature range | Mass loss (%) | Released compound/comment |
|---|---|---|
| 25-250° C. | 15.58 | dioxane |
| 250-350° C. | 14.14 | Decomposition |

Example 7

Preparation of Colchicine Form I

Figure 18:
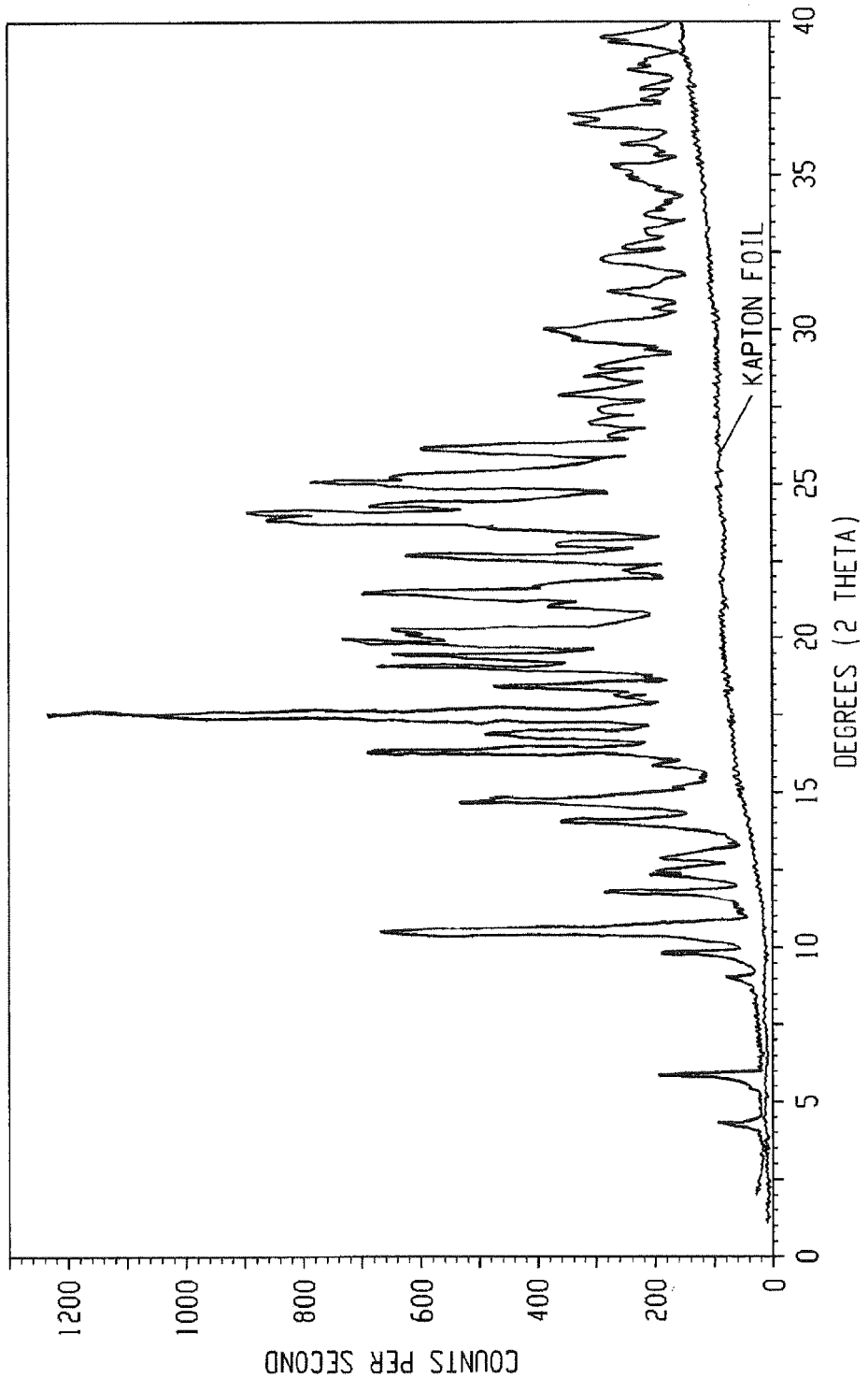
FIG. 18 illustrates XRPD pattern of colchicine Form I.
Figure 19:
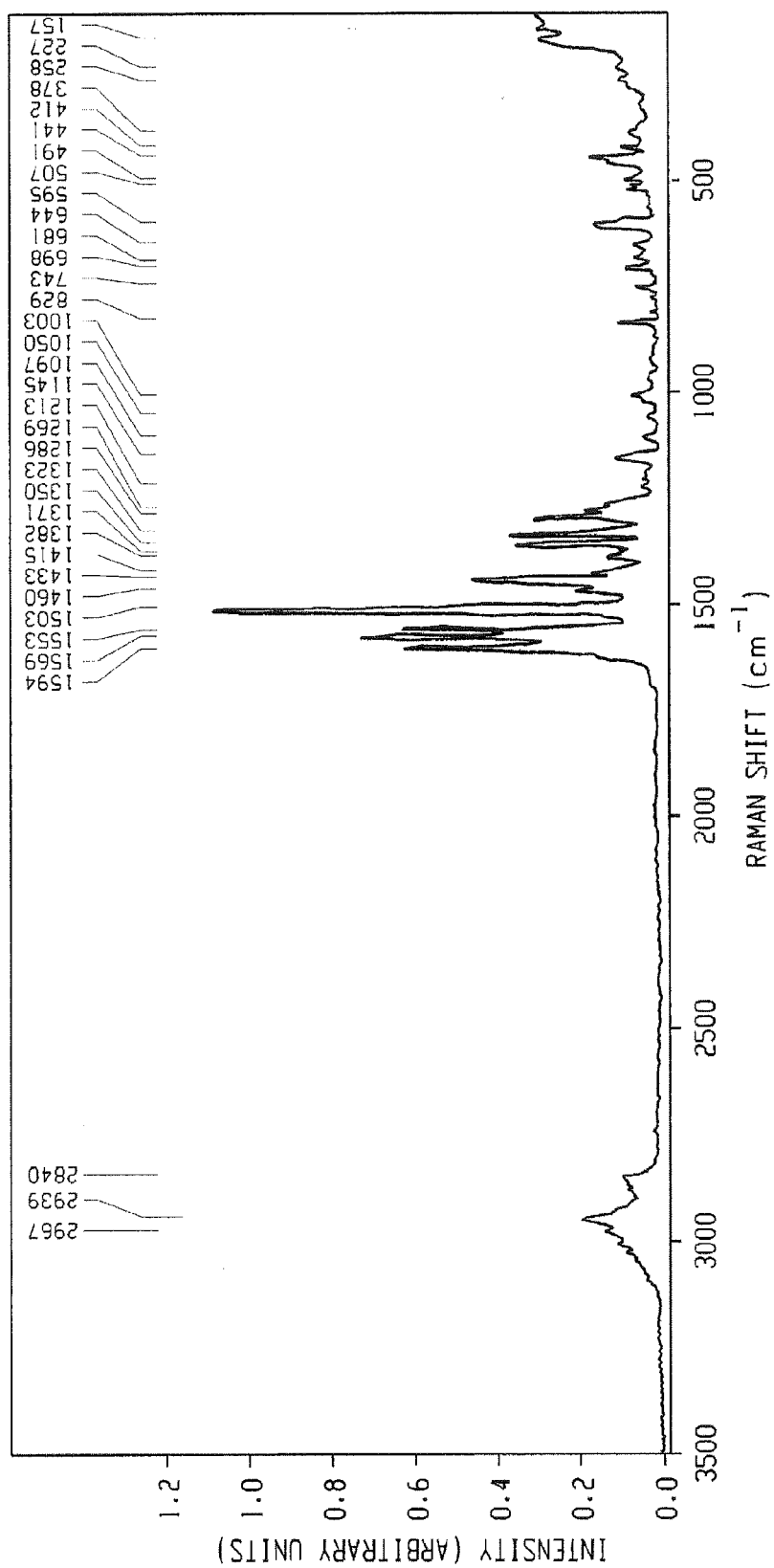
FIG. 19 illustrates a FT-Raman spectrum of colchicine Form I.

A solubility study is run to determine the solubility of colchicine Form A in tetrahydrofuran at room temperature. After several days at 4° C., a precipitate is observed and isolated. 503 mg of colchicine Form A is suspended in 1.0 ml tetrahydrofuran and seeded with the precipitate from the solubility study. The suspension is stirred for 1 day at room temperature forming a very viscous suspension. An additional 0.3 ml tetrahydrofuran is added and the suspension is stirred at room temperature for 1 day, filtered, and dried under ambient conditions for several minutes (268 mg). The material is analyzed by FT-Raman, XRPD, and TG-FTIR. FIG. 18 illustrates an XRPD pattern of Form I with a peak listing provided in Table 21 below. FIG. 19 illustrates a FT-Raman spectrum and a peak listing is provided in Table 21. The analysis indicates the material is a tetrahydrofuran solvate containing about 6.3% solvent.

TABLE 21

XRPD and FT-Raman peak table of colchicine Form I

| XRPD peaks | | FT-Raman peaks |
|---|---|---|
| 2θ [°] | Intensity [%] | (cm$^{-1}$) |
| 4.32 | 7 | 2967 |
| 5.84 | 15 | 2939 |
| 9.02 | 7 | 2840 |
| 9.86 | 16 | 1594 |
| 10.64 | 54 | 1569 |
| 11.74 | 23 | 1553 |
| 12.43 | 17 | 1503 |
| 12.61 | 18 | 1460 |
| 12.97 | 16 | 1433 |
| 14.10 | 30 | 1415 |
| 14.77 | 45 | 1382 |
| 15.91 | 18 | 1371 |
| 16.45 | 56 | 1350 |
| 16.95 | 40 | 1323 |
| 17.61 | 100 | 1286 |
| 18.45 | 39 | — |
| 19.10 | 56 | — |
| 19.45 | 51 | — |
| 19.96 | 61 | — |
| 20.31 | 53 | — |
| 21.06 | 31 | — |
| 21.44 | 56 | — |
| 21.73 | 32 | — |
| 22.21 | 21 | — |
| 22.70 | 51 | — |
| 23.12 | 31 | — |
| 23.94 | 69 | — |
| 24.12 | 77 | — |
| 24.47 | 58 | — |
| 25.10 | 61 | — |
| 25.43 | 51 | — |
| 26.23 | 48 | — |
| 27.04 | 27 | — |
| 27.46 | 25 | — |
| 27.92 | 31 | — |
| 28.51 | 25 | — |
| 28.85 | 26 | — |
| 29.77 | 28 | — |
| 30.09 | 31 | — |
| 31.36 | 23 | — |
| 32.37 | 26 | — |
| 32.80 | 22 | — |
| 33.27 | 18 | — |
| 33.83 | 19 | — |

TG-FTIR analysis reveals a stepwise weight loss of 6.3% tetrahydrofuran which is strongest around 170° C. The results are typical of a solvate (hemisolvate 8.3%; 3:1 colchicine to solvate 5.7%) Decomposition is observed above 270° C.

TABLE 22

| Temperature range | Mass loss (%) | Released compound/comment |
|---|---|---|
| 25-270° C. | 6.28 | THF |
| 270-350° C. | 20.13 | Decomposition |

Example 8

Figure 20:
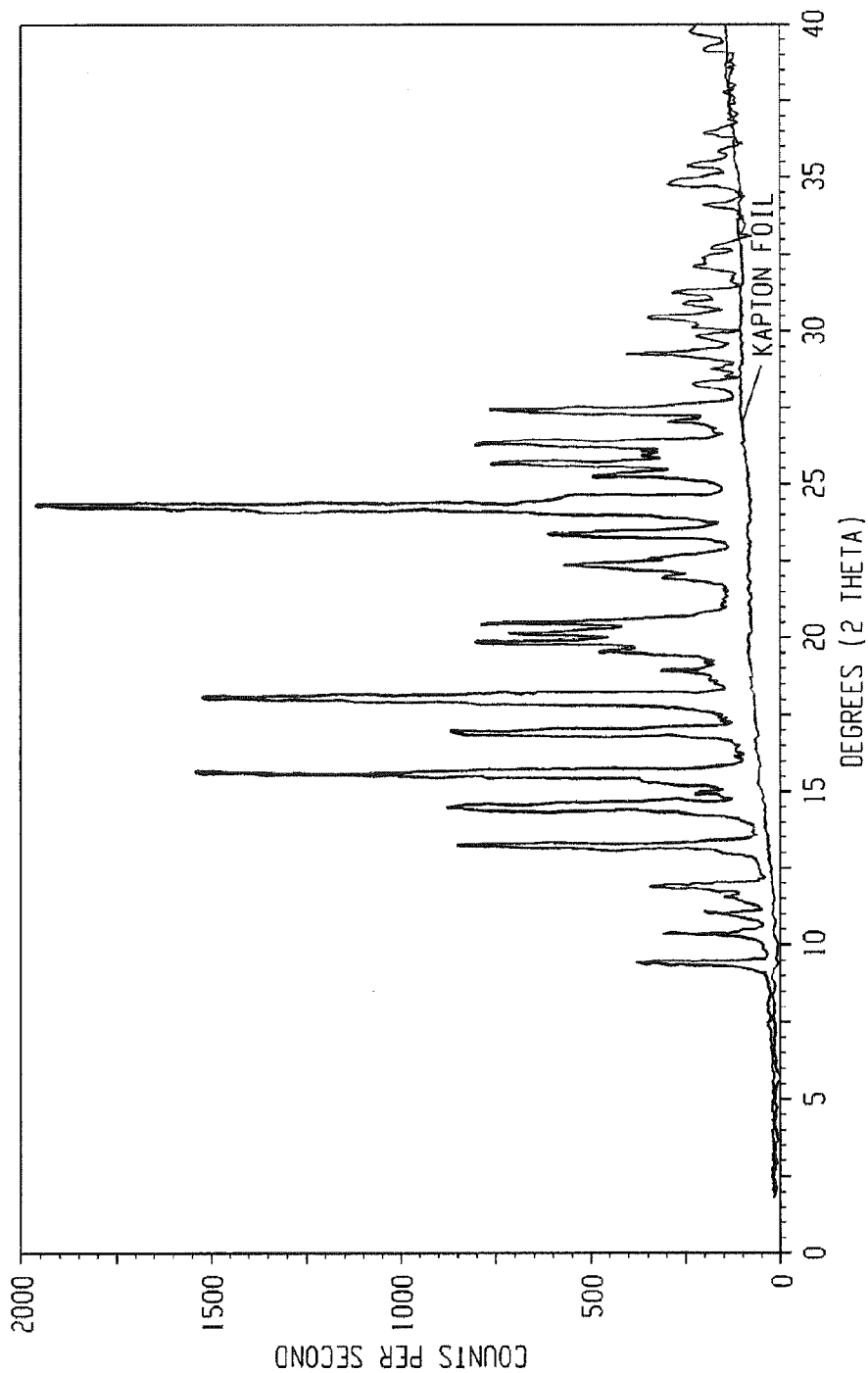
FIG. 20 illustrates XRPD pattern of colchicine Form J.
Figure 21:
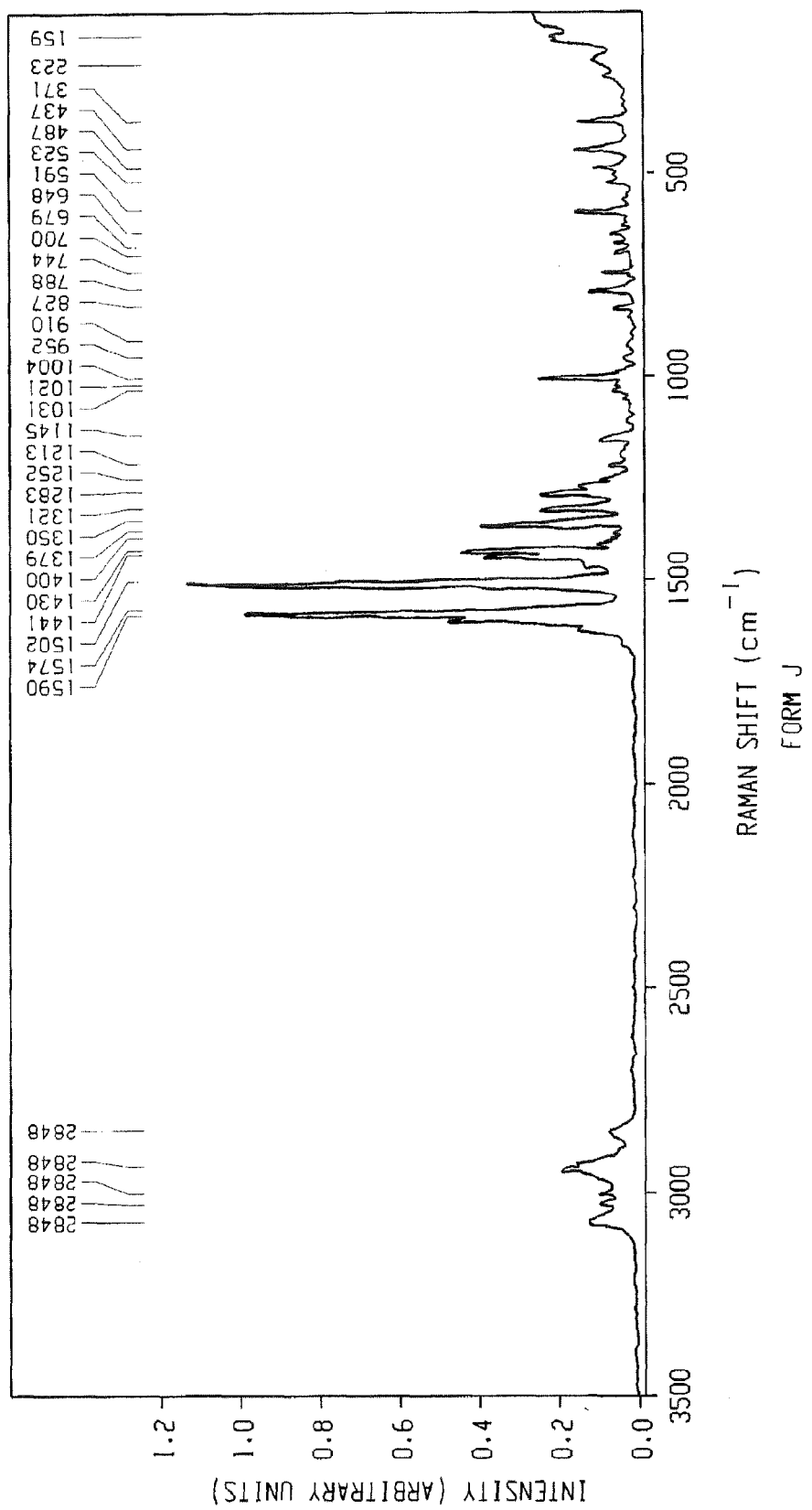
FIG. 21 illustrates a FT-Raman spectrum of colchicine Form J.

Preparation of Colchicine Form J 470 mg of colchicine Form A is suspended in 1.0 ml 3:1 (v/v) toluene/acetonitrile and stirred for 2 days at room temperature, filtered, and dried under ambient conditions for several minutes (297 mg). The material is analyzed by FT-Raman, XRPD, and TG-FTIR. FIG. 20 illustrates an XRPD pattern of Form J with a peak listing provided in Table 23 below. FIG. 21 illustrates a FT-Raman spectrum and a peak listing is provided in Table 23. The analysis indicates the material is a toluene solvate containing about 16.3% solvent.

TABLE 23

XRPD and FT-Raman peak table of colchicine Form J

| XRPD peaks | | FT-Raman peaks |
|---|---|---|
| 2θ [°] | Intensity [%] | (cm$^{-1}$) |
| 9.46 | 19 | 3065 |
| 10.43 | 15 | 3024 |
| 11.11 | 10 | 3002 |
| 11.66 | 7 | 2933 |
| 11.96 | 17 | 2841 |
| 13.27 | 43 | 1590 |
| 14.50 | 41 | 1574 |
| 14.97 | 12 | 1502 |
| 15.67 | 76 | 1441 |
| 17.00 | 44 | 1430 |
| 18.10 | 73 | 1400 |
| 18.98 | 16 | 1379 |
| 19.57 | 23 | 1350 |
| 19.86 | 39 | 1321 |
| 20.15 | 36 | 1283 |
| 20.43 | 41 | 1252 |
| 21.99 | 16 | — |
| 22.31 | 28 | — |
| 22.56 | 17 | — |
| 23.42 | 31 | — |
| 24.26 | 100 | — |
| 24.53 | 28 | — |
| 25.26 | 24 | — |
| 25.62 | 41 | — |
| 26.30 | 42 | — |
| 27.02 | 15 | — |
| 27.42 | 40 | — |
| 28.22 | 12 | — |
| 28.77 | 8 | — |
| 29.24 | 22 | — |
| 29.78 | 11 | — |
| 30.14 | 12 | — |
| 30.42 | 19 | — |
| 30.97 | 13 | — |
| 31.28 | 15 | — |
| 32.13 | 12 | — |
| 32.71 | 10 | — |
| 34.17 | 11 | — |
| 34.79 | 15 | — |

TG-FTIR analysis reveals a stepwise weight loss of 16.3% toluene which is strongest around 160° C. The results are typical of a solvate (monosolvate 18.7%) Decomposition is observed above 240° C.

TABLE 24

| Temperature range | Mass loss (%) | Released compound/comment |
|---|---|---|
| 25-240° C. | 16.27 | toluene |
| 240-350° C. | 12.75 | Decomposition |

Example 9

Figure 22:
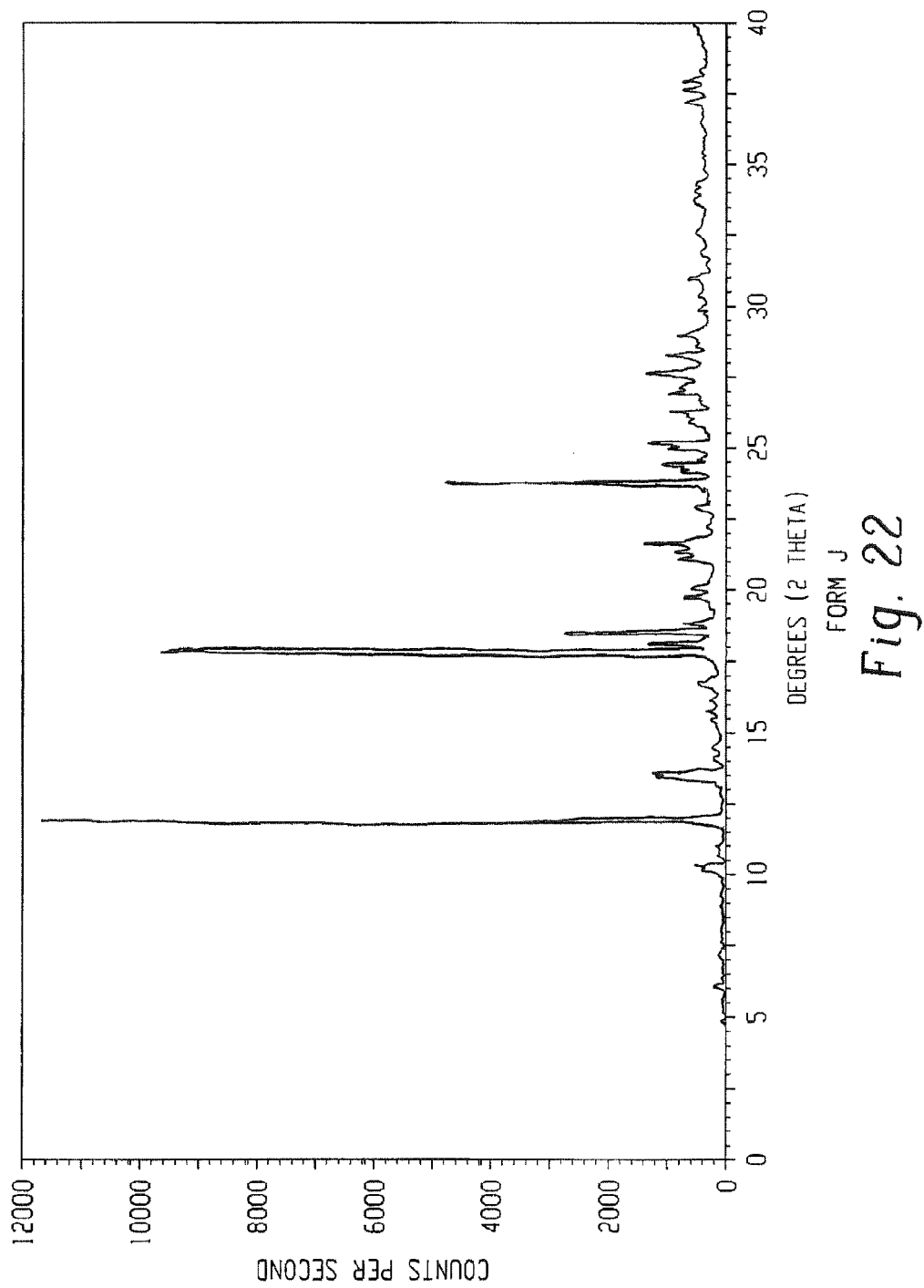
FIG. 22 illustrates XRPD pattern of colchicine Form K.
Figure 23:
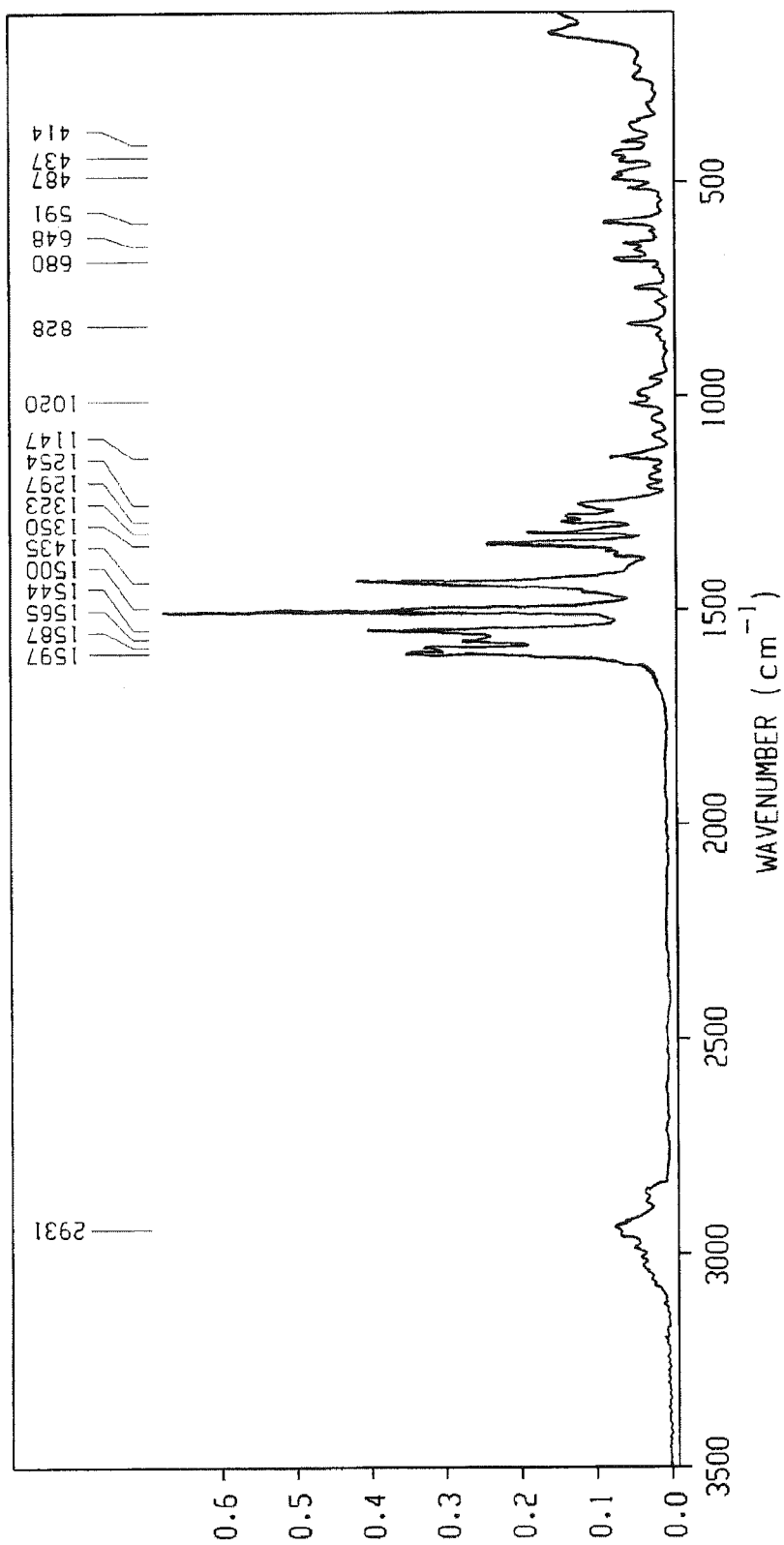
FIG. 23 illustrates a FT-Raman spectrum of colchicine Form K.

Preparation of Colchicine Form K 599 mg of colchicine Form A is dissolved in 30 ml 0.05 M tris(hydroxymethyl)-aminomethane buffer substance pH 7.4 (Fluka, 0.05 M in water). The solution was filtered through a 0.4 micrometer nylon filter. The solvent was allowed to slowly evaporate under nitrogen to 15% of the initial volume (16 days). Large crystals are obtained and analyzed by FT-Raman, XRPD, TG-FTIR, and $^1$H-NMR. FIG. 22 illustrates an XRPD pattern of Form K with a peak listing provided in Table 25 below (it should be noted that it is unknown whether peaks below 5° 2-theta are present). FIG. 23 illustrates a FT-Raman spectrum and a peak listing is provided in Table 25. The analysis indicates the material is probably a hydrate containing 8.7% water.

TABLE 25

XRPD and FT-Raman peak table of colchicine Form K

| XRPD peaks | | FT-Raman peaks |
|---|---|---|
| 2θ [°] | Intensity [%] | (cm$^{-1}$) |
| 6.12 | 2 | 2931 |
| 10.17 | 4 | 2866 |
| 10.32 | 5 | 1597 |
| 11.95 | 100 | 1587 |
| 13.48 | 11 | 1565 |
| 13.59 | 12 | 1544 |
| 14.11 | 2 | 1500 |
| 14.55 | 2 | 1435 |
| 15.47 | 3 | 1350 |
| 15.74 | 3 | 1323 |
| 16.15 | 2 | 1297 |
| 16.79 | 4 | 1285 |
| 17.84 | 86 | 1254 |
| 18.09 | 12 | — |
| 18.52 | 28 | — |
| 18.79 | 7 | — |
| 19.63 | 7 | — |
| 19.95 | 6 | — |
| 21.13 | 8 | — |
| 21.34 | 9 | — |
| 21.61 | 14 | — |
| 21.75 | 8 | — |
| 22.92 | 5 | — |
| 23.78 | 52 | — |
| 24.23 | 8 | — |
| 24.40 | 10 | — |
| 25.01 | 10 | — |
| 25.16 | 14 | — |
| 27.65 | 13 | — |
| 28.26 | 11 | — |
| 28.97 | 8 | — |
| 30.97 | 8 | — |

TG-FTIR analysis on a single crystal reveals a stepwise weight loss of 8.7% water which is strongest around 140° C. The results are typical of a hydrate (dihydrate 8.3%) Decomposition is observed above 250° C.

TABLE 26

| Temperature range | Mass loss (%) | Released compound/comment |
|---|---|---|
| 25-250° C. | 8.71 | water |
| 250-350° C. | 15.46 | Decomposition |

$^1$H-NMR analysis in CDCl$_3$ indicates no peak for tris(hydroxymethyl-aminomethane around 3.2 ppm. However, three additional signals at around 1.6, 1.2, and 0.8 ppm are present for a total of 11 protons indicating the sample contains a substantial amount of another organic compound.

Example 10

Figure 24:
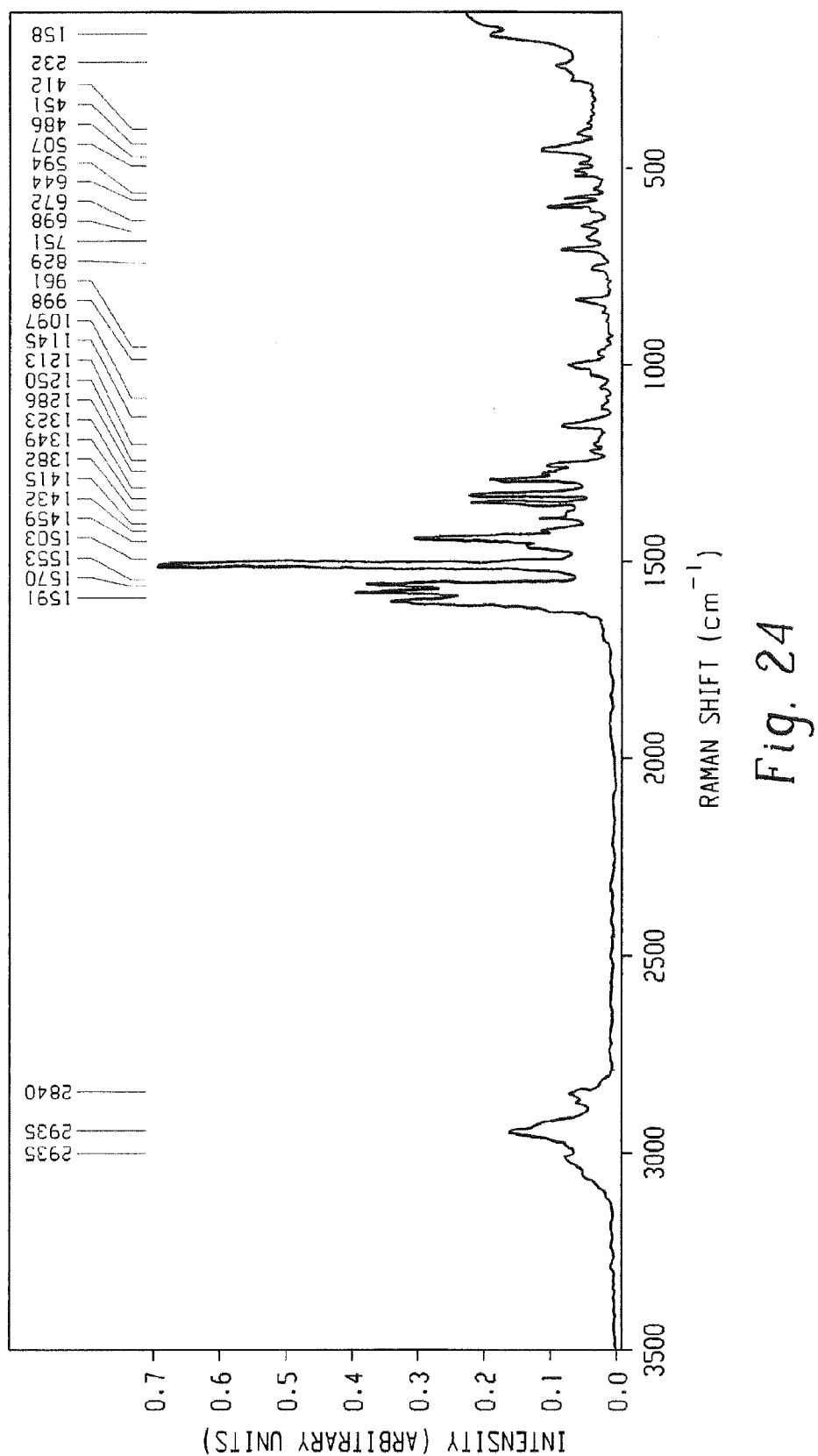
FIG. 24 illustrates a FT-Raman spectrum of colchicine Form L.

Preparation of Colchicine Form L 1.08 g of Form A is suspended in 4 ml 4:1 (v/v) cyclohexane/EtOH, seeded, and stirred at room temperature for 1 day. The resulting material is filtered and shortly dried at ambient conditions. 300 mg of the material is suspended in 3 ml mesitylene and heated to 70° C. to form a yellow gel. The gel is sonicated for 15 minutes at room temperature. The temperature is cycled between 40 and 80° C. for 1 day. The white suspension is heated to 110° C. and dissolved. The resulting material is sonicated for 15 minutes at room temperature and the temperature is cycled between and 80° C. for 1 day. The white material is filtered at 80° C. and dried under nitrogen. The resulting material is analyzed by FT-Raman and TG-FTIR. FIG. 24 illustrates FT-Raman spectrum of colchicine mesitylene solvate with a peak listing provided in Table 27 below. The analysis indicates the material is likely a mesitylene solvate.

TABLE 27

FT-Raman peak table of colchicine Form L
FT-Raman peaks (cm$^{-1}$)

| |
|---|
| 2999 |
| 2935 |
| 2840 |
| 1591 |
| 1570 |
| 1553 |
| 1503 |
| 1459 |
| 1432 |
| 1415 |
| 1382 |
| 1349 |
| 1323 |
| 1286 |

TG-FTIR analysis reveals two stepwise weight losses of a total of 9% mesitylene, which are strongest around 140° C. and 230° C. The results with the second step suggest at least part of the solvent is bound and the material is probably a solvate (6:1 solvate of colchicine to solvent 4.8%; 3:1 solvate of colchicine to solvent 9.1%) Decomposition is observed above 280° C.

TABLE 28

| Temperature range | Mass loss (%) | Released compound/comment |
|---|---|---|
| 25-160° C. | 4.06 | mesitylene |
| 160-280° C. | 4.89 | mesitylene |
| 280-350° C. | 8.84 | Decomposition |

The terms "comprising", "having", "including", and "containing" are to be construed as open-ended terms (i.e., meaning "including, but not limited to"). The terms "a" and "an" do not denote a limitation of quantity, but rather denote the presence of at least one of the referenced item. The term "or" means "and/or". The endpoints of all ranges directed to the same component or property are inclusive and independently combinable.

Unless defined otherwise, technical and scientific terms used herein have the same meaning as is commonly understood by one of skill in the art to which this invention belongs.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating acute gouty arthritis and pain in attacks of acute gouty arthritis, cystic fibrosis, demyelinating diseases of central or peripheral origin, multiple sclerosis, Dupuytren's contracture, idiopathic pulmonary fibrosis, primary amyloidosis, recurrent pericarditis, acute pericarditis, asthma, postpericardiotomy syndrome, Behçet's disease, Familial Mediterranean fever, idiopathic thrombocytopenic purpura, primary biliary cirrhosis, or pyoderma gangrenosum, or prevention of attacks of acute gouty arthritis and pain in attacks of acute gouty arthritis, or chronic gout prophylaxis in a patient, comprising:
   administering to the patient in need thereof a therapeutically effective amount of a colchicine solid state form;
   wherein the colchicine solid state form comprises
   a. Colchicine Form B cyclohexane solvate comprising XRPD peak positions at 5.79, 10.50, 17.47, and 23.86±0.2 degrees 2-theta;
   b. Colchicine Form D ethanol solvate comprising XRPD peak positions at 9.45, 16.26, and 21.16±0.2 degrees 2-theta;
   c. Colchicine Form G acetone solvate comprising XRPD peak positions at 9.39, 16.44, and 18.87±0.2 degrees 2-theta;
   d. Colchicine Form H dioxane solvate comprising XRPD peak positions at 12.04, 15.78, 18.05, and 18.25±0.2 degrees 2-theta;
   e. Colchicine Form I tetrahydrofuran solvate comprising XRPD peak positions at 5.84, 10.64, and 17.61±0.2 degrees 2-theta;
   f. Colchicine Form J toluene solvate comprising XRPD peak positions at 9.46, 15.67, 18.10, and 24.26±0.2 degrees 2-theta; or
   g. Colchicine Form L mesitylene solvate comprising Raman peaks at 2935 and 1503±2 cm$^{-1}$.

2. The method of claim 1, wherein Colchicine Form B cyclohexane solvate comprises XRPD peak positions at 5.79, 10.50, 17.47, and 23.86±0.2 degrees 2-theta.

3. The method of claim 1, wherein Colchicine Form B cyclohexane solvate comprises one or more of the following:
   XRPD peak positions at 5.79, 10.50, 17.47, 19.78, 23.86, and 25.11±0.2 degrees 2-theta; or
   Raman peaks at 2936, 1594, 1571, 1553, and 1503±2 cm-1.

4. The method of claim 1, wherein Colchicine Form D ethanol solvate comprises XRPD peak positions at 9.45, 16.26, and 21.16±0.2 degrees 2-theta.

5. The method of claim 1, wherein Colchicine Form D ethanol solvate comprises one or more of the following:
   XRPD peak positions at 9.45, 16.26, 18.31, 18.76, 21.16, and 25.10±0.2 degrees 2-theta;
   Raman peaks at 2933, 1549, 1501, and 1436±2 cm-1; or
   a melting peak of about 95° C. by DSC analysis.

6. The method of claim 1, wherein Colchicine Form G acetone solvate comprises XRPD peak positions at 9.39, 16.44, and 18.87±0.2 degrees 2-theta.

7. The method of claim 1, wherein Colchicine Form G acetone solvate comprises one or more of the following:
   XRPD peak positions at 9.39, 12.41, 16.44, 18.87, and 20.94±0.2 degrees 2-theta;
   Raman peaks at 2935, 1596, 1559, 1504, and 1431±2 cm-1; or
   a melting peak of about 87° C. by DSC analysis.

8. The method of claim 1, wherein Colchicine Form H dioxane solvate comprises XRPD peak positions at 12.04, 15.78, 18.05, and 18.25±0.2 degrees 2-theta.

9. The method of claim 1, wherein Colchicine Form H dioxane solvate comprises one or more of the following:
   XRPD peak positions at 12.04, 15.78, 18.05, 18.25, 20.35, and 20.59, ±0.2 degrees 2-theta; or
   Raman peaks at 2940, 1573, and 1503±2 cm-1.

10. The method of claim 1, wherein Colchicine Form I tetrahydrofuran solvate comprises XRPD peak positions at 5.84, 10.64, and 17.61±0.2 degrees 2-theta.

11. The method of claim 1, wherein Colchicine Form I tetrahydrofuran solvate comprises one or more of the following:
    XRPD peak positions at 5.84, 10.64, 16.45, 17.61, 23.94, and 24.12±0.2 degrees 2-theta; or
    Raman peaks at 2939, 1594, 1569, 1553, and 1503±2 cm-1.

12. The method of claim 1, wherein Colchicine Form J toluene solvate comprises XRPD peak positions at 9.46, 15.67, 18.10, and 24.26±0.2 degrees 2-theta.

13. The method of claim 1, wherein Colchicine Form J toluene solvate comprises one or more of the following:
    XRPD peak positions at 9.46, 13.27, 14.50, 15.67, 17.00, 18.10, and 24.26±0.2 degrees 2-theta; or
    Raman peaks at 2933, 1590, 1574, and 1502±2 cm-1.

14. The method of claim 1, wherein Colchicine Form L mesitylene solvate comprises Raman peaks at 2935 and 1503±2 cm$^{-1}$.

15. The method of claim 1, wherein Colchicine Form L mesitylene solvate comprises Raman peaks at 2935, 1591, 1570, 1553, and 1503±2 cm-1.

16. The method of claim 1, wherein the colchicine solid state form is formulated into a dosage form further comprising a pharmaceutically acceptable excipient.

* * * * *